(12) United States Patent
Kroll et al.

(10) Patent No.: US 7,668,662 B2
(45) Date of Patent: Feb. 23, 2010

(54) PATIENT-SPECIFIC DOSIMETRY

(75) Inventors: Stewart M. Kroll, Oakland, CA (US); Jeffry A. Siegal, Cherry Hill, NJ (US); Richard L. Wahl, Ann Arbor, MI (US); Kenneth R. Zasadny, Wyandotte, MI (US)

(73) Assignees: The Regents of the University of Michigan, Ann Arbor, MI (US); Smithkline Beecham Corporation, Philadelphia, PA (US)

( * ) Notice: Subject to any disclaimer, the term of this patent is extended or adjusted under 35 U.S.C. 154(b) by 733 days.

(21) Appl. No.: 11/200,688

(22) Filed: Aug. 10, 2005

(65) Prior Publication Data
US 2005/0288869 A1 Dec. 29, 2005

Related U.S. Application Data

(63) Continuation of application No. 09/326,502, filed on Jun. 4, 1999, now abandoned.

(60) Provisional application No. 60/088,327, filed on Jun. 4, 1998.

(51) Int. Cl.
*G06F 19/00* (2006.01)
*A61K 51/00* (2006.01)
*C12P 21/08* (2006.01)

(52) U.S. Cl. .................. 702/19; 424/1.37; 424/1.49; 530/391.3

(58) Field of Classification Search .................. None
See application file for complete search history.

(56) References Cited

U.S. PATENT DOCUMENTS

| 4,831,122 A | 5/1989 | Buchsbaum et al. |
| 6,251,362 B1 | 6/2001 | Wahl et al. |

FOREIGN PATENT DOCUMENTS

| WO | WO-96/34632 | 11/1996 |
| WO | WO-97/42522 | 11/1997 |

OTHER PUBLICATIONS

Benua et al., "The Relation of Radioiodine Dosimetry to Results and Compilations in the Treatment of Metaphysics Thyroid Cancer," Amer. J. Roentg., 87(1): 171-182 (Jan. 1962).
Brownell et al., "Absorbed Fractions for Photon Dosimetry," J. Nuclear Medicine, Supp. 1, MIRD Pamphlet No. 3, pp. 28-39 (Feb. 1968).
Carrasquillo et al., "Radioimmunoscintigraphy of Colon Cancer with Iondine-131-Labeled B72.3 Monoclonal Antibody," J. of Nuclear Medicine, 29: 1022-1030 (Jun. 1988).
Clairand et al., "Dose3D: EGS4 Monte Carlo Code Based Software for International Radionuclide Dosimetry," J. Nuclear Med., vol. 40: 1517-1523 (Sep. 1999).
Colcher et al., "Quantitative Analyses of Selective Radiolabeled Monoclonal Antibody Localization in Metastatic Lesions of Colorectal Cancer Patients," Cancer Research, 47: 1185-1189 (Feb. 15, 1987).
Eary et al., "Iodine-131-Labeled Anti-CD20 (B1) Antibody Therapy for Released Non-Hodgkin's Lymphomas: Phase II Trial Results," The Journal of Nuclear Medicine, Supplemental, 36(5): 214P Abstract No. 963 (May 1995).
Eary et al., "Radioimmunotherapy Treatment Planning Based on Radiation Absorbed Dose or Patient Size," The Journal of Nuclear Medicine, Supplemental, 37(5): 43P, Abstract No. 162 (May 1996).
Ettinger et al., "Phase I-II Study of Isotopic Immunoglobulin Therapy for Primary Liver Cancer," Cancer Treatment Reports, 66(2): 289-297 (Feb. 1982).
Furhang et al., "Thyroid Cancer Dosimetry Using Clearance Fitting," The Journal of Nuclear Medicine, 40(1): 131-136 (Jan. 1999).
Kaminski et al., "Iodine-131-Anti-B1 Radioimmunotherapy for B-cell Lymphoma," Journal of Clinical Oncology, vol. 14: 1974-1981 (Jul. 1996).
Kaminski et al., "Imaging, Dosimetry, and Radioimmunotherapy With Iodine 131-Labeled Anti-CD37 Antibody in B-cell Lymphoma," J. Clinical Oncology, 10(11): 1696-1711 (Nov. 1992).
Kaminski et al., "Radioimmunotherapy of B-cell Lymphoma With (131 I) Anti-B1 (Anti-CD20) Antibody," The New England Journal of Medicine, 329(7): 459-465 (Aug. 12, 1993).
Koral et al., "CT-SPECT Fusion Plus Conjugate Views for Determining Dosimetry in Iodine-131-Monoclonal Antibody Therapy of Lymphoma Patients," The Journal of Nuclear Medicine, 35(10): 1714-1720 (Oct. 1994).
Koral et al., "Preliminary Report of Tumor Dosimetry from I-131 SPECT of Previously-Untreated Patients with B-cell Lymphoma," J. Nuclear Medicine, 39 (5 sppl.): 112P, (May 1998), Abstract No. 437.
Larson et al., "Comparison of Bone Marrow Dosimetry and Toxic Effect of High Dose 131I-Labeled Monoclonal Antibodies Administered to Man," Int. J. Rad. Appl. Instrum. B. 16(2): 153-158 (1989).
Letvin et al., "Use of Radiolabeled Monoclonal Anti-B1 Antibody for B Lymphocyte Imaging in Rhesus Monkeys," Int. J. Rad. Appl. Instrum. B. 14(2): 99-105 (1987).

(Continued)

*Primary Examiner*—Lori A. Clow
(74) *Attorney, Agent, or Firm*—William T. Han, Esq.; Howson & Howson LLP

(57) ABSTRACT

A patient-specific optimally effective radiation dose for administration of a radiopharmaceutical to a patient for treatment of a disease may be established by basing the calculation of the appropriate therapeutic dose on factors such as the desired total body dose, the maximum tolerated dose, the typical clearance profile of the radiopharmaceutical, the patient's mass or maximum effective mass, and the patient-specific residence time of the radiopharmaceutical or an analog in the whole body of the patient. The use of the method allows for treatment of a patient with an appropriate dose which is maximally effective against the disease yet minimally toxic. The determination of a patient-specific therapeutic dose may be assisted by the use of a software program set to the particular parameters of the radiopharmaceutical.

28 Claims, 7 Drawing Sheets

OTHER PUBLICATIONS

Liu et al., "A Radionuclide Therapy Treatment Planning and Dose Estimation System," J. Nuclear Med., 40: 1151-1153 (Jul. 1999).

Loevinger et a;., "A Revised Schema for Calculating the Absorbed Dose from Biologically Distributed Radionuclides," Medical Internal Radiation Dose (MIRD) Committee of the Society of Nuclear Medicine, Pamphlet No. 1, Revised, pp. 3-10 (Mar. 1976).

Malcolm Rowland et al., "Age and Weight" Clinical Pharmacokinetics, Chap. 15, pp. 218-228, Lea & Febiger, Philadelphia, PA, (1980).

Order et al., "Monoclonal Antibodies: Potential Role in Radiation Therapy and Oncology," I. J. Radiation Oncology Bio. Phys., 8: 1193-1201 (Jul. 1982).

Order et al., "Phase I-II Study of Radiolabeled Antibody Integrated in the Treatment of Primary Hepatic Malignacies," I. J. Radiation Oncology Bio. Phys., 6: 703-710 (Jun. 1980).

PK Solutions 2.0 Software, "Noncompartmental Pharmacokinetics Data Analysis," Summit Research Services, Montrose, CO, released Jun. 4, 1997, Online Users Guide.

Rommelfanger et al., "Dosimetry of I-131 Anti-B1 (Anti-CD20) Antibody for Non-Hodgkin's Lymphoma: Comparison of Up-front Treatment vs. Chemotherapy-Refractory Patients," J. Nuclear Medicine, 39 (5 sppl.): 186P, Abstract No. 840 (May 1998).

Schmidt et al., "Whole-Body Kinetics and Dosimetry of L-3-[123I] Iodo-Alpha-Methyltyrosine," European J. Nuclear Medicine, 24(9): 1162-1166, (Sep. 1997).

Siegel et al., "Bone Marrow Dosimetry and Toxicity for Radioimmunotherapy," Antibody, Immunoconjugates, and Radiopharmaceuticals, 3(4): 213-233 (1990).

Siegel et al., "Sacral Scintigraphy for Bone Marrow Dosimetry in Radioimmunotherapy," Int. J. Rad. Appl. Instrum. B., 16(6): 553-559 (1989).

Toohey et al., "Comparative Analysis of Dosimetry Parameters for Nuclear Medicine," Int. Radiopharm. Dosim. Symp. Proc. Conf. Meeting date 1996, 2: 532-551 (1996).

Wahl et al., "Dose Escalation in Radioimmunotherapy Based on Projected Whole Body Dose," J. Nuclear Medicine, 35(5 Sppl): 233P, Abstract No. 952 (1994).

Wahl et al., "Importance of the Terminal Portion of Tumor Time-Activity Curve in Determining Tumor Dosimetry in Radioimmunotherapy," The Journal of Nuclear Medicine, 32(6): 1314-1315 (Jun. 1991).

Wahl et al., "Patient-Specific Whole-Body Dosimetry: Principles and a Simplified Method for Clinical Implementation," J. Nuclear Medicine., 39(8 Spll.): 14S-20S, (Aug. 1998).

Wahl et al., "Radioimmunotherapy with I-131-Anti-B-1 for Refractory B-cell Lymphoma: Updated Phase I Study Results," The Journal of Nuclear Medicine, Supplemental, 36(5): 214P, Abstract No. 961 (May 1995).

Weinstein et al., "Monoclonal Antibodies in the Lymphatics: Toward the Diagnosis and Therapy of Tumor Metastases," Science, 218: 1334-1337 (Dec. 24, 1982).

Zasadny et al., "A Simplified Method for Determining Therapeutic Activity to Administer for Radioimmunotherapy," The Journal of Nuclear Medicine, Supplemental, 37 (5): 43P, Abstract No. 163 (May 1996).

Zasadny et al., "Correlation of Dosimetric Parameters with Hematological Toxicity after Radioimmunotherapy of Non-Hodgkin's Lymphoma with I-131 Anti-B1. Utility of a New Parameter: 'Total Body Dose-Lean'," The Journal of Nuclear Medicine, Supplemental, 36(5): 214P, Abstract No. 962 (May 1995).

Zasadny et al., "Standardized Uptake Values of Normal Tissues at PET with 2-[Fluorine-18]-Fluoro-2-deoxy-D-glucose: Variations with Body Weight and a Method for Correction," Radiology, 189(3): 847-850 (Dec. 1993).

Document RSICC Code Package CCC-528, "MIRDOSE 3.1: Code System That Calculates Internal Dose Estimates by the MIRD Technique," retrieved from http://www-rsicc.ornl.gov/codes/ccc/ccc5/ccc-528.html on Aug. 30, 2001. Abstract dated Mar. 1988, May 1995, Apr. 1998.

PATIENT-SPECIFIC DOSIMETRY

CROSS-REFERENCE TO RELATED APPLICATION

This application is a continuation of U.S. patent application Ser. No. 09/326,502, filed Jun. 4, 1999, now abandoned, which claims the benefit under 35 USC §119(e) of U.S. Provisional Application No. 60/088,327, filed Jun. 4, 1998.

STATEMENT REGARDING FEDERALLY SPONSORED RESEARCH OR DEVELOPMENT

This invention was supported in part by NIH Grants CA56794 and CA42768. The U.S. Government may have rights in this invention.

BACKGROUND OF THE INVENTION

The invention relates to methods of optimizing the therapeutic dose of a radiopharmaceutical to be given to a patient for treatment of a disease.

Radiopharmaceuticals are becoming more widely used for the treatment of disease in patients. Research continues, however, to elucidate the specifics of how to most effectively utilize radiopharmaceuticals in therapy. For example, the optimally effective administered activity of the radiopharmaceutical for any given radiopharmaceutical is not immediately evident. There is a substantial variance among patients in how long radiopharmaceuticals are retained in the body, so that a patient who retains a given radiopharmaceutical for a long time will get a much higher radiation dose than a similar-sized patient who retains the given radiopharmaceutical for a shorter period of time. This is not predictable from patient weight or body surface area alone. With varying clearance rates of any given radiopharmaceutical, differing radiation doses would be delivered to each patient per millicurie of the radiopharmaceutical administered, even if the patients have identical masses or body surface areas.

When conventional methods of dosing are used, e.g., simply based on the patient's size, there is the potential for causing adverse effects, on the one hand, and failing to provide an effective dose, on the other hand. Overdosing with the radiopharmaceutical may have dire consequences including damage to normal tissues, myeloablation, and death. Myeloablation typically necessitates hematopoietic stem cell reintroduction (usually a bone marrow transplant) in order for the patient to recover hematopoietic function. This is often an undesirable further procedure, especially in the treatment of seriously ill patients. Underdosing of the radiopharmaceutical is also not desired. If a standard dose below the known toxicity level for the particular radiopharmaceutical is given to each patient, then some patients may get enough radioactivity for treatment of the disease, but many others will not get enough. Repeat dosing is not a practicable alternative because of cost, resource, and patient general health considerations. Furthermore, it is extremely difficult to predict whether a certain patient in whom little or no effect has been seen with the standard therapy dose should be given a repeat dose, since the poor results may be due to some other physiological factors. If a repeat therapy dose is desired, it is difficult to ascertain how long after the initial dose the repeat dose should be administered and whether the repeat dose should be at full strength or a fraction of the initial dose.

Thus, it is highly desirable to adjust for these variabilities on an individual patient basis. Patient-specific dosimetry that takes into account the individual patient's pharmacokinetics and the radiation energy absorbed within the whole body of the patient is needed to determine the most appropriate dose for the individual patient.

BRIEF SUMMARY OF THE INVENTION

The invention is a simplified dosimetric approach of general clinical and research applicability for treatment of patients with radiopharmaceuticals, and is based on patient-specific characteristics.

The invention is a method of establishing an optimally effective dose for administration of a radiopharmaceutical to a patient for treatment of disease. The method is based on various aspects of the radiopharmaceutical and how it acts within the body of the patient. Thus, patient-specific characteristics, such as patient body mass and pharmacokinetics, and more general characteristics based on the radionuclide of the radiopharmaceutical are taken into account.

Other aspects of the invention include a computer software program or a computer system for implementing the method.

DETAILED DESCRIPTION OF THE INVENTION

Figure 1:
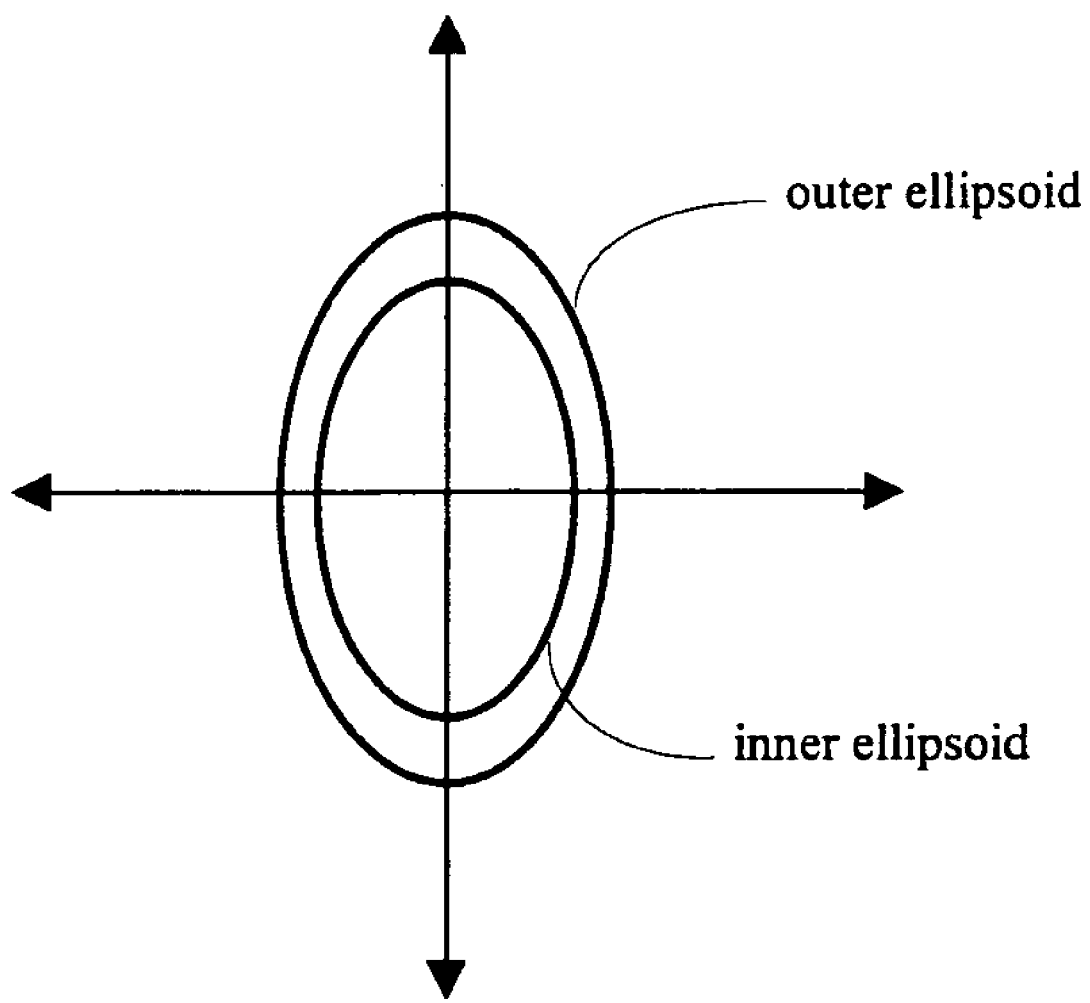
FIG. 1 illustrates the relationship of the fat component of the individual with respect to the lean component of the same individual, thus defining the "lean person (inner ellipsoid) within the fat person (outer ellipsoid)" theory of the present invention.
Figure 2:
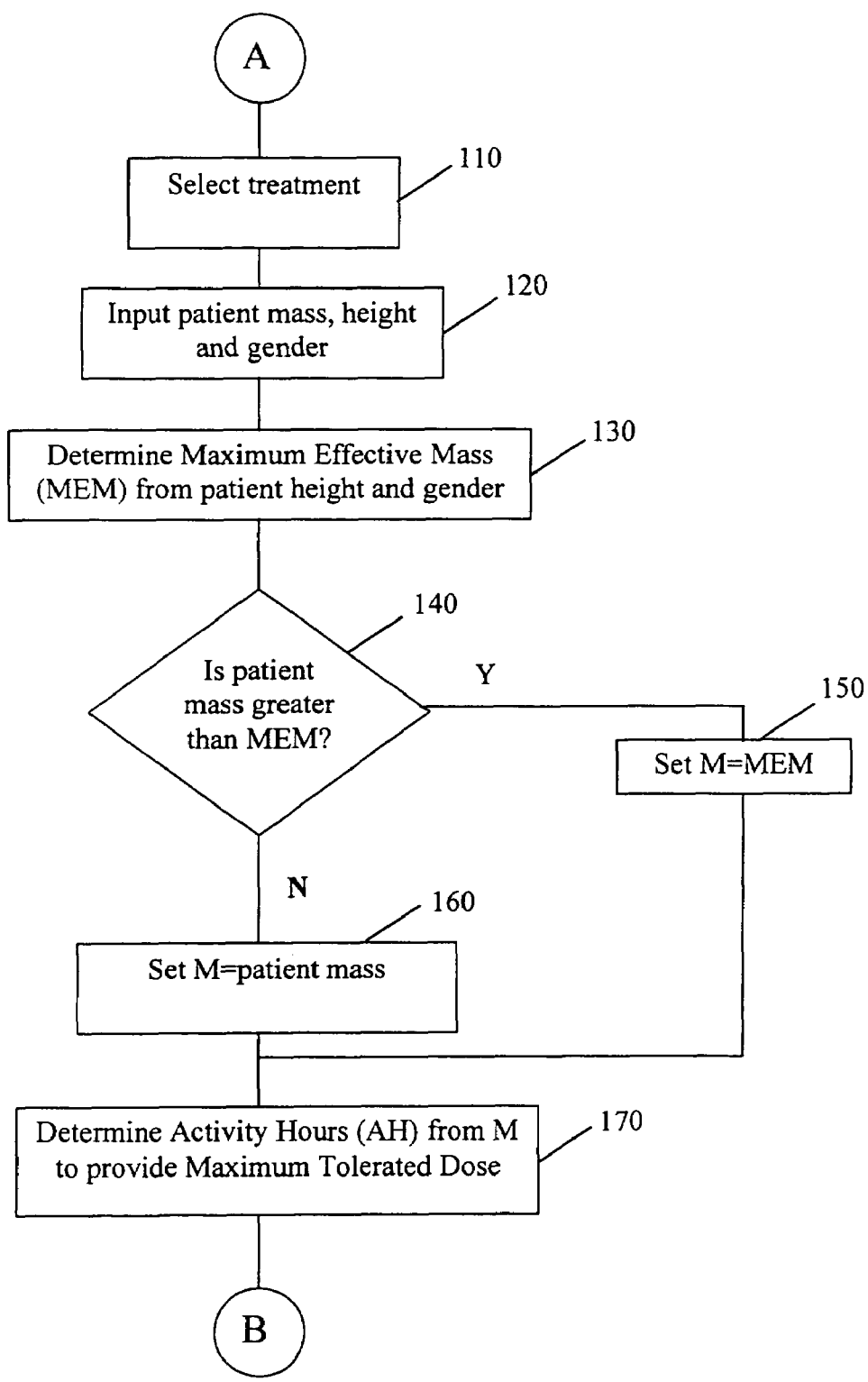
FIG. 2 is a flowchart for the implementation of the methods of the invention in a computer system.

Abbreviations:
AH means activity hours;
cGy means centigray, one cGy is equivalent to one rad;
mCi means millicurie;
MEM means maximum effective mass;
MTD means maximum tolerated dose; and
TBD means total body dose.

Patient-specific dosimetry is used for calculating the optimally effective dose of a radiopharmaceutical to be administered to a patient in the methods of the invention. This is a significant improvement over previous dosimetry methods, since it allows the radiation dose to be tailored to the specific physiological characteristics, including pharmacokinetics, of the individual patient. Patient-specific dosimetry provides the advantages of maximized efficacy and minimized toxicity. Performance of the data acquisition and calculation steps for the patient-specific dosimetry methods is not burdensome, but may be further assisted by a computer.

The patient-specific dosimetry taught herein is a simplified method for determining the therapeutic dose of a radiopharmaceutical to be administered to an individual patient and involves the following two steps: (a) administration of a dosimetric dose of the radiopharmaceutical or its analog followed by sequential measurement of the elimination kinetics of the dosimetric dose, preferably with an appropriately collimated and calibrated gamma camera, or other suitable apparatus, operated in whole body scanning mode (serial anterior and posterior whole body scans), and (b) calculation of the therapeutic dose to be administered to the individual patient. The therapeutic dose of the radiopharmaceutical can then be administered to the patient according to the prescribed protocol for treatment of the disease.

In order to establish a patient-specific optimal effective radiation dose, initially, one needs to gather certain data on the individual patient and the radiopharmaceutical, and then this information is combined with information regarding the desired absorbed total body dose for treatment of the specific disease. More specifically, the activity hours, or cumulated activity, measured in units of millicurie hours, for the radiopharmaceutical is determined based on a combination of patient-specific factors (such as the patient's mass or maximum effective mass and the desired total body dose) and general characteristics of the radionuclide. A dosimetric evaluation is then performed on the patient, usually with the use of a lower millicurie amount of the radiopharmaceutical, to get an understanding of the rate at which the radiopharmaceutical is cleared from the patient's body. The dosimetric evaluation provides an indication of the residence time of the radiopharmaceutical for the individual patient. The activity hours are then combined with the residence time and optionally adjusted via an attenuation factor in order to establish the optimum therapeutic dose in millicurie units for treatment of the individual patient.

Radiopharmaceutical

The radiopharmaceutical is usually a radioimmunoconjugate, typically an antibody or antibody fragment conjugated to a radiolabel for delivery to a specific target within the body of the patient. The term "radiopharmaceutical" more broadly encompasses any radioactively-labeled targeting moiety, directed to a target within the body. Thus, although immunoconjugates are of great value in therapy, the conjugate with which the patient will be treated may have something other than an immunologically active molecule as the targeting moiety. For example, as used herein, the radiopharmaceutical may be a ligand for a receptor. "Radiopharmaceutical" may be even more broadly defined as any pharmaceutical associated with or comprising a radionuclide. The pharmaceutical may be associated with a radionuclide through a chelator, direct chemical bonding, or some other means. The radiopharmaceutical may also consist essentially of a radionuclide. For example, $^{89}$Sr is used as a radiopharmaceutical for the treatment of bone pain and Na$^{131}$I is used as a radiopharmaceutical for the treatment of thyroid cancer. Although neither of these radiopharmaceuticals is specifically attached to a targeting moiety, each is highly useful because it tends to accumulate in the organ in which treatment is desired.

While radiopharmaceuticals that move to certain specific sites within the body unassisted or that are made to be directed to the specific sites are most widely used for therapy, administered radiopharmaceuticals which act systemically or in a non-targeting fashion, e.g. to treat metastatic foci throughout the body, may also be used in patient treatment. Calculation of the optimally effective dose for treatment with all radiopharmaceuticals according to the methods of the present invention is advantageous so that treatment efficacy is maximized and toxicity is minimized. Thus, the methods of patient-specific dosimetry taught herein may be used for radiopharmaceuticals generally.

In the practice of the methods of the invention, the radiopharmaceutical to be eventually administered to the patient for treatment or an analog of the radiopharmaceutical may be used at the dosimetric evaluation stage. Generally, a single radiopharmaceutical, usually radiolabeled in differing amounts (typically a high millicurie amount for delivery of a therapeutically effective amount of radioactivity and a relatively small millicurie amount for the earlier dosimetric evaluation) is used for patient-specific dosimetry and for treatment. If a radiopharmaceutical analog is to be used, it should be predictive of the residence time of the radiopharmaceutical in the body of the patient. By way of example, the radiopharmaceutical analog may differ from the radiopharmaceutical of interest by virtue of having a different radiolabel (e.g., the radiopharmaceutical may be a particular antibody labeled with $^{90}$Y whereas the radiopharmaceutical analog may be the same antibody labeled with $^{111}$In), or it may be of a different size (such as an antibody fragment), or the radiolabel may be conjugated to the targeting moiety in a different manner in the analog. Further, the analog may be a type of molecule or particle distinct from the radiopharmaceutical, such as an artificial particle or optically traceable (and non-radioactive) agent for measurement of the patient's clearance rate. The analog should be suitable, however, for use in the dosimetric evaluation, so it should predict therapeutic behavior of the radiopharmaceutical.

Radionuclides

The methods of the present invention may be used without limitation to the type of radionuclide that is included in the radiopharmaceutical, although those radionuclides having greatest utility in a method of treatment of the patient and in a method of establishing the optimally effective dose for treatment will be those that meet certain criteria. These criteria generally include high therapeutic value, ready availability, a physical half-life within a practicable range for dosimetric evaluation and treatment of the patient, and good imaging qualities, either of the radionuclide itself or of an acceptable analog. Radionuclides that emit β particles, photons (x-rays and γ emissions), α particles, Auger electrons, and/or internal conversion electrons or any other emission may be used. A gamma or positron-emitter is preferably used for the dosimetric evaluation. The methods may be advantageously used to optimize dosing for a broad range of radionuclides including $^{111}$In, $^{67}$Ga, $^{90}$Y, $^{131}$I, $^{125}$I, $^{123}$I, $^{32}$P, $^{47}$Sc, $^{67}$Cu, $^{109}$Pd, $^{111}$Ag, $^{153}$Sm, $^{166}$Ho, $^{177}$Lu, $^{186}$Re, $^{188}$Re, $^{199}$Au, $^{211}$At, $^{212}$Bi, $^{233}$Ra, $^{225}$Ac, $^{213}$Bi, and $^{99m}$Tc.

The methods taught herein are particularly appropriate for $^{131}$I-labeled radiopharmaceuticals as $^{131}$I is a combined beta and gamma emitter. The gamma photon from $^{131}$I decay, although of high energy, is easily detectable by gamma scintigraphy or a NaI (thyroid) probe. Both methods are suitable for determining the rate of clearance of the tracer from the body of the patient.

The use of other radionuclides may require some adjustment to the simplest form of practicing the invention, however. For example, $^{90}$Y emits beta particles and little to no gamma radiation, with the result that a radiopharmaceutical having a $^{90}$Y radiolabel may be difficult to image via conventional means, such as the typical gamma camera available in hospital nuclear medicine facilities. Imaging of a $^{90}$Y-labeled radiopharmaceutical may occur, however, using the Bremsstrahlung emissions from the $^{90}$Y radionuclide. Alternatively, an analog for the radiopharmaceutical may be used at the dosimetric evaluation stage of the methods of the invention. A form of the radiopharmaceutical that is radiolabeled with $^{111}$In, a radionuclide which is relatively easy to image via conventional means, may be used as a substitute for the $^{90}$Y-labeled radiopharmaceutical, for example, so that the $^{111}$In-labeled radiopharmaceutical analog may be used to predict the residence time in the patient of the therapeutically effective $^{90}$Y-labeled radiopharmaceutical. Similarly, the positron-emitter $^{124}$I might be used to predict residence time for $^{131}$I therapies. Further, a radiopharmaceutical having an α-emitter, such as bismuth, may be used, but "imaging" at the dosimetric evaluation stage may then comprise blood or urine sampling and counting of the samples to determine the patient-specific residence time.

The methods of the present invention are typically practiced using radiopharmaceuticals, and specifically radionuclides, that are not substantially deposited in the bone or bone marrow since avoidance of myeloablation is generally an important aim in the therapy. As will be evident to practitioners in the field, however, deposition of the radionuclide in the bone may be desired (e.g., $^{89}$Sr treatment for bone pain) or an acceptable side effect (e.g., where the treatment is supported by bone marrow transplant) for the treatment of certain diseases or disease states. Therefore, the invention may be utilized to optimize dosing even for radiopharmaceuticals that are deposited in the bone or bone marrow.

Maximum Tolerated Dose

The maximum tolerated dose (MTD) is usually defined by reference to the relevant patient subpopulation. Typically, one can determine the MTD by doing a dose escalation study for the specific radiopharmaceutical of interest in the patient subpopulation.

For example, the patient population may be all patients having a certain disease, such as non-Hodgkin's lymphoma, defined broadly or narrowly depending on the characteristics of the disease. The patient subgroup or subpopulation in this example may be patients who are refractory to the usual chemotherapy regimen for non-Hodgkin's lymphoma or perhaps patients who are above a certain age, have low platelet counts, or are immunocompromised due to certain factors. The more narrowly one defines the patient subpopulation to gather useful data on the MTD, the greater confidence that the specific patient to be treated will be given the appropriate and optimally effective radiation dose.

Of course, it is possible to establish an MTD for the patient who is actually to be treated, e.g. via an estimation within the judgment of the physician, typically with consideration given to the patient's history and teachings in the relevant field, although the MTD is more usually defined by reference to other patients who have a similar disease profile. The actual MTD for the specific patient under treatment, for obvious reasons, is difficult to establish in a de novo patient since the goals of establishing the specific MTD for the patient and treating the patient with a patient-specific optimally effective dose may be at odds.

Once the patient subpopulation is defined, the MTD is established, typically through a dose escalation study. For example, the MTD was established as a 75 cGy total body dose for chemotherapy relapsed/refractory patients with non-Hodgkin's lymphoma (Kaminski, M. S. et al., "Iodine-131-Anti-B1 Radioimmunotherapy for B-cell Lymphoma," *J. Clin. Oncol.*, 14:1974-1981 (1996)). Thus, in the methods of the invention, the step of determining the MTD may comprise performing a dose escalation study for the radiopharmaceutical in a patient subpopulation.

The MTD may be set differently for different patient groups, or the value may be considered a different desired total body dose (TBD), discussed in further detail below, for a particular patient subgroup. For example, a dose of 75 cGy to the whole body may be established in a given patient population (e.g., all patients with non-Hodgkin's lymphoma who are refractory to chemotherapy) as the MTD via a dose escalation study, but then be attenuated for a patient with low platelet counts to 65 cGy. Thus, the 65 cGy may be considered the desired TBD for a patient within a subgroup of the population (e.g., all patients with non-Hodgkin's lymphoma who are refractory to chemotherapy and who have low platelet count). Alternatively, the MTD may be established, as by a separate dose escalation study, in a population of patients that is defined as all patients with non-Hodgkin's lymphoma who are refractory to chemotherapy and who have low platelet counts. Then, a particular patient may have a desired TBD equal to the MTD. In any case, it is evident that TBD/MTD represents an attenuation factor that is preferably multiplied by the activity hours/residence time for the particular patient to be treated with the radiopharmaceutical.

Total Body Dose

The desired TBD is determined for the patient and may be based on information on the patient population or subpopulation or it may be specific to the individual patient, within the judgment of the physician. The value for TBD is generally equal to or lesser than the MTD.

Measurement of the clearance rate and determination of the desired TBD for treatment of the patient is a more significant predictor of toxicity and appropriate therapeutic dose than the patient's body weight or surface area. Thus, calculation of an actual mCi amount of therapeutic dose for the patient, with a variety of patient-specific factors taken into account, is more potent than simply performing a mCi/kg or mCi/m$^2$ calculation.

Whole body dosimetry, which focuses on the absorbed dose in the whole body of the patient, is a simpler and more appropriate focus than organ dosimetry. It is an accurate, precise, and reproducible approach to treatment of the patient. Organ dosimetry, on the other hand, requires multiple views, the often highly subjective practice of drawing of regions of interest around organs, estimates of organ volume, calculation of fractional energy deposition in organs, difficult to correct background counts, attenuation correction, and scatter correction.

Even though the bone marrow may be the expected target organ for radiation-induced toxicity of a particular radiopharmaceutical, it is feasible to focus the data acquisition on the whole body of the patient. Bone marrow dosimetric estimates are generally difficult to obtain, especially if there are any malignant cells admixed with the normal bone marrow elements. Although bone marrow dosimetry calculations from gamma scans have been performed, they are particularly challenging in patients with high-bulk lymphoma, as the lymphoma often involves the lymph nodes overlying marrow, making planar imaging-based estimation of bone marrow dose difficult or impossible. While precisely quantitated single photon emission computed tomography (SPECT) images may address this, the methods of the invention, focused on the whole body of the patient, provides the necessary data for a reliably optimized therapeutic dose.

The whole body dosimetry approach of the invention is based on a model that assumes the radiopharmaceutical is distributed uniformly throughout the patient's lean body portion following administration and remains so. This homogeneous model is clearly a simpler and more workable model than heterogeneous models, as it requires only a single whole body radiation activity input value per time point making it extremely suitable for a prospective dosimetric method.

Clearance Profile

Information on the clearance profile, or usual pattern of clearance, of the radiopharmaceutical from humans to whom it has been administered is useful in the methods of the invention. Specifically, the clearance profile of the radiopharmaceutical indicates whether the radiopharmaceutical clears in a generally straight line, i.e. according to a monoexponential profile, or whether the radiopharmaceutical clears according a more complicated pattern. "Clearing" or "clearance" of the radiopharmaceutical as used herein refers to the process of diminishment of radioactivity within the patient's body over time, whether through normal physiological functions, such as elimination of the radiopharmaceutical from the body, or natural decay of the radionuclide.

Knowledge of the typical clearance profile for the radiopharmaceutical is useful to determine, e.g. if the radiopharmaceutical clears according to a monoexponential profile (with one slope, basically a straight line), a biexponential profile (two slopes), a triexponential profile (three slopes), etc. This information becomes useful in determining how many data points should be gathered for a high degree of confidence at the step of determining the residence time of the radiopharmaceutical. In other words, one can more accurately gauge the appropriate, usually the minimum feasible, number of data points if the usual clearance profile of the radiopharmaceutical or its analog is known. Two to three data points per exponential term are generally sufficient. If there is monoexponential clearance, for example, 2-3 data points may be sufficient for a high degree of confidence in the resulting calculations. For a radiopharmaceutical that clears biexponentially, measurement at 4-6 data points is preferred. For a radiopharmaceutical that clears triexponentially, measurement at 6-9 data points is preferred. Although data may be gathered at a higher number of points, it is convenient to know the minimum number recommended for an acceptable level of confidence in the results.

If clearance profile information for the radiopharmaceutical is unavailable, one may calculate a therapeutic dose for the patient by assuming that the radiopharmaceutical clears in a monoexponential pattern, given the fact that a majority of radiopharmaceuticals clear in this manner. It is preferable to get an actual clearance profile of the radiopharmaceutical, however, for greatest confidence in the results.

The clearance profile may be dependent on a number of factors including the specificity and affinity of the radiopharmaceutical to its target, the size of the radiopharmaceutical, and the species of origin (e.g., a murine antibody given to a human patient will clear differently than a human or humanized antibody will clear in the human patient).

The step of determining the clearance profile may comprise performing a simple study of the radiopharmaceutical in a given patient subpopulation, such as administration of the radiopharmaceutical followed by simple measurement overtime of the loss of radioactivity. Although determination of the clearance profile in humans is preferred, clearance profile information gathered from an animal model is also useful. A dose escalation study, such as that described above with reference to establishing an MTD, is also useful for an indication of the clearance profile of the radiopharmaceutical of interest. Further, the usefulness of an radiopharmaceutical analog was discussed above with reference to the dosimetric evaluation of the individual patient. Similarly, an analog of the radiopharmaceutical may be used to determine the clearance profile.

It should be understood that "clearance profile" as used herein refers to a general characteristic of the radiopharmaceutical in patients, i.e., the shape of the activity-time curve. This is distinct from the step of determining the residence time, discussed below, which refers to the time the activity of the radiopharmaceutical remains in the individual patient. Thus, the step of determining the residence time incorporates the concept of measuring the clearance rate of the radiopharmaceutical or its analog in the individual patient, whereas the step of determining the clearance profile is generally based on information gathered from other than the individual patient.

Although "determining" has been used in reference to the step of utilizing the clearance profile of the radiopharmaceutical, it will be evident that such data may be gathered from historical sources, such as published literature or other knowledge available to one of skill in the relevant field, and not just by actually performing the step of establishing the clearance profile at the time that the individual patient's needs are addressed. Thus, one may have determined the clearance profile of the radiopharmaceutical by reference to published data from a prior time and then presently be utilizing such information in the method of establishing the optimal patient-specific dose for treatment of the patient. There is no requirement in the methods of the invention of timing of the step of determining the clearance profile; i.e., no requirement of when or by whom the clearance profile is determined. Similarly, there are no such limitations on the steps of determining a maximum tolerated dose and a desired total body dose for the radiopharmaceutical.

Maximum Effective Mass

Preferably, the methods of the present invention take into account any adjustments that may be necessary due to obesity of the patient. The concept of focusing on the patient's lean body mass or maximum effective mass (MEM) represents a departure from the usual approaches to dosimetry and is based on the theory that the human body represents two major compartments, a "fat" compartment and a "lean" compartment residing within the fat compartment. Distribution of the radiopharmaceutical is not uniform throughout the patient's body. Little accumulation of the radiopharmaceutical actually occurs in the fat compartment. The bone marrow, which is especially susceptible to toxicities related to treatment with radiopharmaceuticals, is part of the lean compartment, according to this theory. Thus, if a patient, and especially an obese patient, is dosed simply based on mass, e.g. on a mCi/kg basis, then there is the potential for overdosing the patient and ablating the bone marrow. A more appropriate model is that the radioactivity is distributed uniformly mostly within the lean component of the patient's body.

FIG. 1 illustrates the relationship of the fat and lean components of the individual patient, generally represented as superimposed ellipsoids. The outer ellipsoid, with the larger x and y dimensions, represents fat plus lean body mass. The inner ellipsoid with the same aspect ratios, is defined (in kg), where height is measured in centimeters, by the following formulae:

Males: 48.0+1.06(height−152)=Lean Body Mass

Females: 45.5+0.91(height−152)=Lean Body Mass.

It is understood that lean body mass may also be directly measured by computerized tomography, x-ray absorptiometry, immersion weighing, and other known methods. The total body absorbed dose is then determined for the lean body ellipsoid, assuming the MTD was established for the lean body mass. Corrections for Compton scatter of photons from the fat compartment or some trace accumulation in the fat compartment are also possible (e.g., Monte Carlo simulations of radiation scatter and reabsorption may be performed for the fat and lean components), but need not be included in the simplest calculation of the lean body mass.

It follows that a calculation of the portion of the patient which is "lean body mass" should be used for an accurate determination of the appropriate dose to be given to the patient at the treatment stage. Alternatively, the patient's MEM may be determined, for this purpose. In the case of one particular radiopharmaceutical, the MEM was defined as 1.37 times the lean body mass, based on empirical data gathered from dose escalation studies in the patient population. A fair approximation of the MEM for treatment purposes with the particular radiopharmaceutical may then be generated from the given formulas (with the slight modification of 1.37× lean body mass) and put in tabular form, as seen in Table 1, for example, or may be incorporated into a software program. Once the table is generated for the particular radiopharmaceutical, one need not calculate the lean body mass for each patient, but instead may refer to the table, taking the patient's gender and height into account, to find the MEM and then use the lower of the actual mass (M) of the patient or the MEM in further calculations.

TABLE 1

Maximum Effective Mass for $^{131}$I-Labeled Anti-B1 Radiopharmaceutical

| | Men | | | Women | |
|---|---|---|---|---|---|
| Height (ft, in) | Height (cm) | Maximum Effective Mass (kg) | Height (ft. in) | Height (cm) | Maximum Effective Mass (kg) |
| 4'5" | 134.5 | 40.5 | 4'5" | 134.5 | 40.7 |
| 4'6" | 137.0 | 44.2 | 4'6" | 137.0 | 43.8 |
| 4'7" | 140.0 | 47.9 | 4'7" | 140.0 | 47.0 |
| 4'8" | 142.0 | 51.6 | 4'8" | 142.0 | 50.2 |
| 4'9" | 145.0 | 55.3 | 4'9" | 145.0 | 53.3 |
| 4'10" | 147.5 | 59.0 | 4'10" | 147.5 | 56.5 |
| 4'11" | 150.0 | 62.7 | 4'11" | 150.0 | 59.7 |
| 5'0" | 152.5 | 66.3 | 5'0" | 152.5 | 62.8 |
| 5'1" | 155.0 | 70.0 | 5'1" | 155.0 | 66.0 |
| 5'2" | 157.5 | 73.7 | 5'2" | 157.5 | 69.2 |
| 5'3" | 160.0 | 77.4 | 5'3" | 160.0 | 72.3 |
| 5'4" | 162.5 | 81.1 | 5'4" | 162.5 | 75.5 |
| 5'5" | 165.0 | 84.8 | 5'5" | 165.0 | 78.7 |
| 5'6" | 167.5 | 88.5 | 5'6" | 167.5 | 81.8 |
| 5'7" | 170.0 | 92.2 | 5'7" | 170.0 | 85.0 |
| 5'8" | 172.5 | 95.8 | 5'8" | 172.5 | 88.2 |
| 5'9" | 175.5 | 99.5 | 5'9" | 175.5 | 91.3 |
| 5'10" | 178.0 | 103.2 | 5'10" | 178.0 | 94.5 |
| 5'11" | 180.5 | 106.9 | 5'11" | 180.5 | 97.7 |
| 6'0" | 183.0 | 110.6 | 6'0" | 183.0 | 100.8 |
| 6'1" | 185.5 | 114.3 | 6'1" | 185.5 | 104.0 |
| 6'2" | 188.0 | 118.0 | 6'2" | 188.0 | 107.2 |
| 6'3" | 190.5 | 121.7 | 6'3" | 190.5 | 110.3 |
| 6'4" | 193.0 | 125.4 | 6'4" | 193.0 | 113.5 |
| 6'5" | 195.5 | 129.0 | 6'5" | 195.5 | 116.7 |
| 6'6" | 198.0 | 132.7 | 6'6" | 198.0 | 119.8 |
| 6'7" | 200.5 | 136.4 | 6'7" | 200.5 | 123.0 |
| 6'8" | 203.0 | 140.0 | 6'8" | 203.0 | 126.2 |
| 6'9" | 205.5 | 143.8 | 6'9" | 205.5 | 129.3 |
| 6'10" | 208.5 | 147.5 | 6'10" | 208.5 | 132.5 |
| 6'11" | 211.0 | 151.2 | 6'11" | 211.0 | 135.7 |
| 7'0" | 213.5 | 154.9 | 7'0" | 213.5 | 138.8 |

Multiply lb by 0.454 to determine kg.
Multiply in by 2.54 to determine cm.
To calculate the maximum effective mass for patient heights not included in above table use the following formulas (18):
Men: MEM (kg) = 65.76 + 1.452 (ht in cm − 152)
Women: MEM (kg) = 62.34 + 1.247 (ht in cm − 152).

Thus, the lean body mass or MEM of the patient is preferably determined to account for the nonhomogeneous biodistribution of radioactivity in obese patients. Patients weighing in excess of the maximum effective mass may then be treated with a dose of the radiopharmaceutical calculated based on the maximum effective mass. Patients having a mass less than the determined maximum effective mass may have their therapeutic dose calculated based on their actual body mass. By first estimating what fraction of the body is lean and then calculating the radioactivity distribution within a given body mass, the proper dose of radiopharmaceutical for treatment without undue toxicity can be administered on an individualized, case-by-case basis.

Activity Hours

Once the patient's maximum effective mass is determined, e.g. through the use of the information provided in Table 1, then the lower of the patient's M or MEM is used in the determination of the activity hours to deliver the desired total body dose.

The activity hours ("AH" in the equation), also known as cumulated activity, for the radiopharmaceutical are determined based on a combination of patient-specific factors (such as the M or MEM and the desired TBD) and general characteristics of the radionuclide. The AH is measured in units of millicurie hours (mCi·hr) and is defined by Equation I as follows:

$$AH = \frac{TBD \times (M \text{ or } MEM)}{\left[\sum_{elec} \Delta_{elect} + \sum_{phot} \Delta_{phot} \phi_{phot}^{TB}\right]}. \quad \text{(Equation I)}$$

The bracketed portion of the equation represents the sum of electron energy plus photon energy deposited in the patient's total body and will vary depending on the radionuclide used and the patient's mass. Thus, for each radionuclide, using the equation above along with published data, such as that obtained from MIRD pamphlets, one can generate tables or create databases that are dependent on the radionuclide and the patient and, which will provide an indication of the activity hours needed to deliver a desired total body dose to the patient. This avoids the need to do repeated calculations.

For example, if it is known that 75 cGy of a particular $^{131}$I-labeled antibody is of therapeutic value, one can substitute 75 cGy for the total body dose (TBD) in the equation above, generate the bracketed portion of the equation based on characteristics of the patient and the particular radionuclide, in this case $^{131}$I, and simply need to input the individual patient's M or MEM to determine the activity hours needed to obtain the desired TBD.

Equation I is simply the desired TBD (i.e., 75 cGy) divided by the total body S-value since the total body S-value (as opposed to organ-specific S-value) for the patient is the bracketed term in Equation I divided by the M or MEM. The S-value is the absorbed dose per unit cumulated activity. S-values calculated using this approach are based on the actual patient M or MEM rather than using a standardized mass of some anthropomorphic model. Thus, these S-values, and therefore the activity hours, are patient-specific. Notably, the patient-specific residence time, discussed in detail below, multiplied by the total body S-value, gives the therapeutic dose in units of cGy/mCi.

Table 2 is an example of a look-up table for determining the activity hours needed to deliver a dose of 75 cGy of $^{131}$I to the whole body of the patient, based on the patient's M or MEM. The values in Table 2 were generated with the aid of published data. Specifically, assuming that the patient is "ellipsoid" in shape, absorbed fractions of $^{131}$I photon energy deposited in an ellipsoid of principal axes ratios of 1/1.8/9.27 for various masses were calculated from Medical Internal Radiation Dose (MIRD) Pamphlet No. 3, Table 9 (Brownell, G. L., et al.,

*Absorbed fractions for photon dosimetry, Soc. Nucl. Med.*; MIRD Pamphlet No. 3:Table 9 (1968)) and the mean energy emitted per nuclear transition was obtained from the $^{131}$I decay scheme data in MIRD Pamphlet No. 10 (Dillman, L. T., et al., *Radionuclide decay schemes and nuclear parameters for use in radiation-dose estimation, Soc. Nucl. Med*, MIRD Pamphlet No. 10 (11975)). The total body S-values using these two parameters and this approach for a wide range of patient masses were compared to S-values from the MIR-DOSE 3.1 program and showed very close agreement over a wide range of patient total body masses. It is evident that one may also, or alternatively, generate a table of S-values (cGy/mCi·hr) rather than activity hours, which would not have information on the patient's TBD. An adjustment to account for the patient's TBD could easily be made once the appropriate S-value is determined for treatment of the patient. Similarly, one may wish to generate a table of activity hours or S-values based on the $\Delta_{elect}$, $\Delta_{phot}$, and $\phi^{TB}_{phot}$ values using a different model for the particular radionuclide. In particular situations, the tables may be eliminated altogether and only the patient's M or MEM may be used since, e.g., for $^{131}$I the activity hours are a slowly varying function of mass. It is possible to multiply the patient's M or MEM by AH/kg or an AH/kg function (obtained from analysis of the AH/kg vs. kg curve).

TABLE 2

Activity Hours to Deliver a 75 cGy Total Body Radiation Dose of $^{131}$I

| M or MEM [1] (kg) | Activity Hours (mCi hr) |
|---|---|
| 40.0 | 4638 |
| 40.5 | 4690 |
| 41.0 | 4743 |
| 41.5 | 4796 |
| 42.0 | 4848 |
| 42.5 | 4901 |
| 43.0 | 4953 |
| 43.5 | 5005 |
| 44.0 | 5057 |
| 44.5 | 5109 |
| 45.0 | 5160 |
| 45.5 | 5212 |
| 46.0 | 5264 |
| 46.5 | 5315 |
| 47.0 | 5366 |
| 47.5 | 5413 |
| 48.0 | 5469 |
| 48.5 | 5520 |
| 49.0 | 5571 |
| 49.5 | 5621 |
| 50.0 | 5672 |
| 50.5 | S724 |
| 51.0 | 5775 |
| 51.5 | S826 |
| 52.0' | 5878 |
| 52.5 | 5929 |
| 53.0 | 5980 |
| 53.5 | 6031 |
| 54.0 | 6082 |
| 54.5 | 6133 |
| 55.0 | 6184 |
| 55.5 | 6234 |
| 56.0 | 6285 |
| 56.5 | 6335 |
| 57.0 | 6386 |
| 57.5 | 6436 |
| 58.0 | 6486 |
| 58.5 | 6536 |
| 59.0 | 6586 |
| 59.5 | 6636 |
| 60.0 | 6686 |
| 60.5 | 6737 |
| 61.0 | 6787 |
| 61.5 | 6838 |
| 62.0 | 6888 |
| 62.5 | 6938 |
| 63.0 | 6989 |
| 63.5 | 7039 |
| 64.0 | 7089 |
| 64.5 | 7139 |
| 65.0 | 7189 |
| 65.5 | 7238 |
| 66.0 | 7288 |
| 66.5 | 7338 |
| 67.0 | 7387 |
| 67.5 | 7437 |
| 68.0 | 7486 |
| 68.5 | 7536 |
| 69.0 | 7585 |
| 69.5 | 7634 |
| 70.0 | 7683 |
| 70.5 | 7733 |
| 71.0 | 7783 |
| 71.5 | 7833 |
| 72.0 | 7883 |
| 72.5 | 7932 |
| 73.0 | 7982 |
| 73.5 | 8031 |
| 74.0 | 8081 |
| 74.5 | 8130 |
| 75.0 | 8180 |
| 75.5 | 8229 |
| 76.0 | 8278 |
| 76.5 | 8327 |
| 77.0 | 8376 |
| 77.5 | 8425 |
| 78.0 | 8474 |
| 78.5 | 8523 |
| 79.0 | 8572 |
| 79.5 | 8621 |
| 80.0 | 8670 |
| 80.5 | 8718 |
| 81.0 | 8767 |
| 81.5 | 8816 |
| 82.0 | 8864 |
| 82.5 | 8913 |
| 83.0 | 8961 |
| 83.5 | 9010 |
| 84.0 | 9058 |
| 84.5 | 9106 |
| 85.0 | 9154 |
| 85.5 | 9202 |
| 86.0 | 9251 |
| 86.5 | 9299 |
| 87.0 | 9347 |
| 87.5 | 9394 |
| 88.0 | 9442 |
| 88.5 | 9490 |
| 89.0 | 9538 |
| 89.5 | 9585 |
| 90.0 | 9633 |
| 90.5 | 9682 |
| 91.0 | 9730 |
| 91.5 | 9779 |
| 92.0 | 9827 |
| 92.5 | 9875 |
| 93.0 | 9924 |
| 93.5 | 9972 |
| 94.0 | 10020 |
| 94.5 | 10068 |
| 95.0 | 10117 |
| 95.5 | 10165 |
| 96.0 | 10213 |
| 96.5 | 10261 |

TABLE 2-continued

Activity Hours to Deliver a 75 cGy
Total Body Radiation Dose of $^{131}$I

| M or MEM [1] (kg) | Activity Hours (mCi hr) |
|---|---|
| 97.0 | 10309 |
| 97.5 | 10357 |
| 98.0 | 10404 |
| 98.5 | 10452 |
| 99.0 | 10500 |
| 99.5 | 10548 |
| 100.0 | 10595 |
| 100.5 | 10643 |
| 101.0 | 10690 |
| 101.5 | 10738 |
| 102.0 | 10785 |
| 102.5 | 10833 |
| 103.0 | 10880 |
| 103.5 | 10927 |
| 104.0 | 10975 |
| 104.5 | 11022 |
| 105.0 | 11069 |
| 105.5 | 11116 |
| 106.0 | 11163 |
| 106.5 | 11210 |
| 107.0 | 11257 |
| 107.5 | 11304 |
| 108.0 | 11351 |
| 108.5 | 11398 |
| 109.0 | 11445 |
| 109.5 | 11492 |
| 110.0 | 11538 |
| 110.5 | 11585 |
| 111.0 | 11632 |
| 111.5 | 11678 |
| 112.0 | 11725 |
| 112.5 | 11771 |
| 113.0 | 11818 |
| 113.5 | 11864 |
| 114.0 | 11910 |
| 114.5 | 11957 |
| 115.0 | 12003 |
| 115.5 | 12049 |
| 116.0 | 12095 |
| 116.5 | 12141 |
| 117.0 | 12187 |
| 117.5 | 12233 |
| 118.0 | 12279 |
| 118.5 | 12325 |
| 119.0 | 12371 |
| 119.5 | 12417 |
| 120.0 | 12463 |
| 120.5 | 12509 |
| 121.0 | 12556 |
| 121.5 | 12602 |
| 122.0 | 12648 |
| 122.5 | 12694 |
| 123.0 | 12741 |
| 123.5 | 12787 |
| 124.0 | 12833 |
| 124.5 | 12879 |
| 125.0 | 12925 |
| 125.5 | 12971 |
| 126.0 | 13017 |
| 126.5 | 13063 |
| 127.0 | 13109 |
| 127.5 | 13155 |
| 128.0 | 13200 |
| 128.5 | 13246 |
| 129.0 | 13292 |
| 129.5 | 13337 |
| 130.0 | 13383 |
| 130.5 | 13429 |
| 131.0 | 13474 |
| 131.5 | 13520 |
| 132.0 | 13565 |
| 132.5 | 13611 |
| 133.0 | 13656 |
| 133.5 | 13701 |
| 134.0 | 13747 |
| 134.5 | 13792 |
| 135.0 | 13837 |
| 135.5 | 13882 |
| 136.0 | 13928 |
| 136.5 | 13973 |
| 137.0 | 14018 |
| 137.5 | 14063 |
| 138.0 | 14108 |
| 138.5 | 14153 |
| 139.0 | 14198 |
| 139.5 | 14242 |

[1] Minimum of the patient's actual mass (M) (kg) or maximum effective mass (MEM) (kg). For values between 140 kg and 160 kg use the following formula:
Activity hours (mCi hr) = 14287 + (88.74) (mass in kg − 140).

For patients below 40 kg or above 160 kg, Equation I may be applied, with an appropriate adjustment for $\phi^{TB}_{phot}$.

If one is consistently using the methods of the present invention to tailor a patient-specific therapeutic dose for a particular radiopharmaceutical and the desired TBD for all of the patients to be treated is also consistent, then a look-up table, such as Table 2, set for the particular radiopharmaceutical and desired TBD, is a useful tool in the practice of the invention. Alternatively, one can easily put the information regarding the activity hours needed to deliver any desired TBD of a particular radionuclide to a patient into a database, so that only the patient's M or MEM and the desired TBD need to be entered into a software program designed to access the database, to generate the number of needed activity hours. The use of software and the generation of databases on activity hours are especially advantageous if one is working with several different radionuclides or several different desired total body doses, and a variety of patient masses.

Dosimetric Evaluation

Since it is difficult to predict exactly how an individual patient will react to the radiopharmaceutical, a dosimetric evaluation is performed to calculate the appropriate amount of the therapeutic dose of the radiopharmaceutical.

Dosimetric evaluation is generally useful for measuring biodistribution and looking at localization of the radiopharmaceutical within the body of the patient. Primarily, however, its value in the methods of the present invention is for measuring the rate of clearance, particularly the residence time, of the radiopharmaceutical in the total body of the individual patient. Although the typical clearance profile for the radiopharmaceutical is preferably known at the time of treating the individual patient, the rate of clearance of the radiopharmaceutical is specific to the individual patient.

Generally, a tracer dose of the radiopharmaceutical, labeled with an amount of the radionuclide sufficient to gather imaging or count data, but not necessarily of a therapeutic level, is given to the patient at the dosimetric evaluation stage. Thus, an $^{131}$I-labeled radiopharmaceutical of 0.5-10 mCi may be used at the dosimetric stage and the same $^{131}$I-labeled radiopharmaceutical may be used at a dose of 10-400 mCi for treatment of the patient for disease. Although the radiopharmaceutical to be used at the therapeutic stage may be used at the dosimetric stage, a suitable analog may also be used within the judgment of those of skill in the art. For example, the therapeutic radiopharmaceutical may be an $^{90}$Y-labeled monoclonal antibody and the radiopharmaceutical analog suitable as a tracer for dosimetric evaluation may be an $^{111}$In-labeled version of the same monoclonal antibody.

The tracer is preferably administered to the patient intravenously, although other means for administering pharmaceuticals to patients may be used.

Imaging

The type of emissions from the radionuclide portion of the radiopharmaceutical will determine the best means for imaging the tracer at the dosimetric evaluation stage. For example, $^{131}$I is a combined beta and gamma particle emitter. The gamma photons from $^{131}$I decay, although of high energy, are easily detectable by gamma scintigraphy or thyroid probe. Since $^{90}$Y is primarily a beta emitter, either an analog (such as an $^{111}$In-labeled version of the radiopharmaceutical) can be used at the dosimetric stage, as discussed above, or a properly calibrated instrument suitable for the radionuclide, such as a gamma camera or thyroid probe that measures Bremsstrahlung emissions of $^{90}$Y, may be used.

More typically, however, a probe, such as a collimated sodium iodide probe (for example, Picker Model 1 thyroid probe) is useful for obtaining information for the dosimetric evaluation. Alternatively, a gamma camera having either a single-head or dual-head configuration may be used. Both methods appear to be suitable for determining the rate of total body clearance of the tracer and comparable results have been obtained.

The gamma camera is equipped with a collimator suitable for the radionuclide. In the case of an $^{131}$I-labeled radiopharmaceutical, the gamma camera is preferably a large or an extra large field of view and is equipped with a medium- or high-energy parallel hole collimator suitable for performing whole body scans and whole body counts. While patient-specific total body dosimetry may be performed by whole body camera passes or probe measurements, consideration should be given to using a conjugate view probe approach in each patient as it generally requires less time. For example, anterior and posterior probe counts may take only two minutes for image acquisition per data point whereas gamma camera whole body passes may require twenty minutes. In many cases, however, the use of anterior or posterior (or lateral or oblique) body counts may be sufficient for a high degree of confidence, so that a conjugate view is not strictly necessary.

It is important to note that "imaging" as used herein, denotes any activity that allows for the gathering of counting data on the tracer. An actual visual image, while often desirable for following the localization of the radiopharmaceutical, is not strictly necessary. Thus, "imaging" for the purpose of carrying out the methods of the invention includes the use of equipment which provides data of a primarily numeric value, as well as that which provides visual images. Further, imaging includes gathering data on the clearance profile of the radiopharmaceutical via blood or urine sampling at the various time points and counting the radioactivity of the samples, e.g. via a calibrated well counter or a liquid scintillation counter.

Quality control of the equipment is important. Further, images of the same duration should be made at each time point of the dosimetric evaluation, preferably using the same camera, collimator, and other equipment. Thus, camera and probe sensitivity should ideally be checked each day prior to obtaining the patient whole body counts. A liquid or solid source of a calibrated amount of the radionuclide is preferably scanned to determine the counting efficiency (background corrected CPM/μCi). This step assures that the probe or camera parameters, such as the same collimator, scanning speed, window setting, and geometry, are maintained at each imaging time point.

Residence Time

An understanding of the amount of time that the radiopharmaceutical remains within the patient's body to provide a therapeutic, but not unduly toxic, effect is important to optimal dosing. Radiopharmaceuticals clear from the human body at different rates based on the individual's unique physiological characteristics. In fact, the inventors of the dosimetry approach taught herein have found that patients of similar size may have a two- to five-fold difference in clearance rate. Thus, it is highly advantageous to perform a dosimetric evaluation on the patient prior to therapy with the radiopharmaceutical. Dosimetric evaluation with the radiopharmaceutical (usually a dose having a smaller amount of radioactivity) or an appropriate analog thereof determines the individual patient's residence time for use in calculation of the therapeutic dose of the radiopharmaceutical yet to be administered.

The time course of radioactivity clearance in the patient of an administered dosimetric or tracer dose of the radiopharmaceutical or of a radiopharmaceutical analog is followed via the pre-therapy dosimetric evaluation. Typically, a lower millicurie amount of the radiopharmaceutical than will actually be administered at a therapeutic stage is administered to the patient during the dosimetric evaluation, then the level of radioactivity within the patient is measured by means of imaging to determine the percent injected activity at the first time point. This is followed by measurement of the percent injected activity at later time points for elucidation of the clearance rate of the radiopharmaceutical in the individual patient. As can be expected, the percent injected activity is approximately 100% at the first time point, or it may be normalized to 100%. Information on the radioactivity (i.e., counting data) within the patient's body at later time points is then adjusted with reference to the first time point, so that each later time point is a percentage of the first time point. For greater accuracy, each measured time point is preferably background corrected so that radioactivity levels in the environment not originating from the patient may be eliminated from consideration.

More specifically, to determine the residence time in hours, the patient is administered the dosimetric dose, typically via intravenous infusion, on Day 0. At time point 1, usually within a reasonable time, such as one hour, after infusion of the radiopharmaceutical or analog, and before the patient excretes the radioactivity, radioactivity counts are obtained via imaging. Time point 1 is actually calculated from the start of the infusion to the time of image acquisition on Day 0.

The background corrected total body count at the time point (defined as the geometric mean of the anterior and posterior counts after the respective background counts have been subtracted) is then calculated as follows:

$$\text{Background corrected count} = \sqrt{(C_A - C_{BA})(C_P - C_{BP})}. \quad \text{(Equation II)}$$

In this equation, $C_A$=the anterior counts, $C_{BA}$=the anterior background counts. $C_P$=the posterior counts, and $C_{BP}$=the posterior background counts. It is notable that counts obtained from only a single projection per time point generally result in equivalent residence times as those obtained from conjugate anterior and posterior images. Therefore, for single head cameras, total body residence times may be calculated using only anterior counts. In the equation above, therefore, only the anterior background corrected counts ($C_A-C_{BA}$) would be used.

Imaging or radioactivity count acquisition is repeated at the later time points in the same manner. The total number and frequency of the data points is dependent on the anticipated clearance profile, e.g. $^{131}$I-anti-B1 clears in a monoexponential pattern considering both elimination and the physical decay of the radionuclide. Thus, for a particular $^{131}$I-labeled radiopharmaceutical, for example, data was gathered at three time points, Day 0, Day 2, 3, or 4, and Day 6 or 7. These time points were selected as appropriate because the radiopharmaceutical had a monoexponential clearance profile (so data acquisition at three time points is within sound judgment) and a physical half-life of 8 days (so measurements are properly spaced at approximately time zero, a time close to the physical half-life, and an intermediate time). As discussed above with respect to gathering information on the typical clearance profile of the radiopharmaceutical, correlation of the number of time points to the clearance pattern is preferred so that at least 2 time point measurements are made if the radiopharmaceutical has monoexponential clearance, at least 4 time point measurements are made if the radioimmunoconjugate has biexponential clearance, and at least 6 measurements are made if the radioimmunoconjugate has triexponential clearance, etc. Of course, the recommended number and frequency of data points to obtain a calculated therapeutic dose for the particular radiopharmaceutical with a high degree of confidence may be adjusted within the judgment of the physician or other health care personnel on a case-by-case basis.

Figure 7:
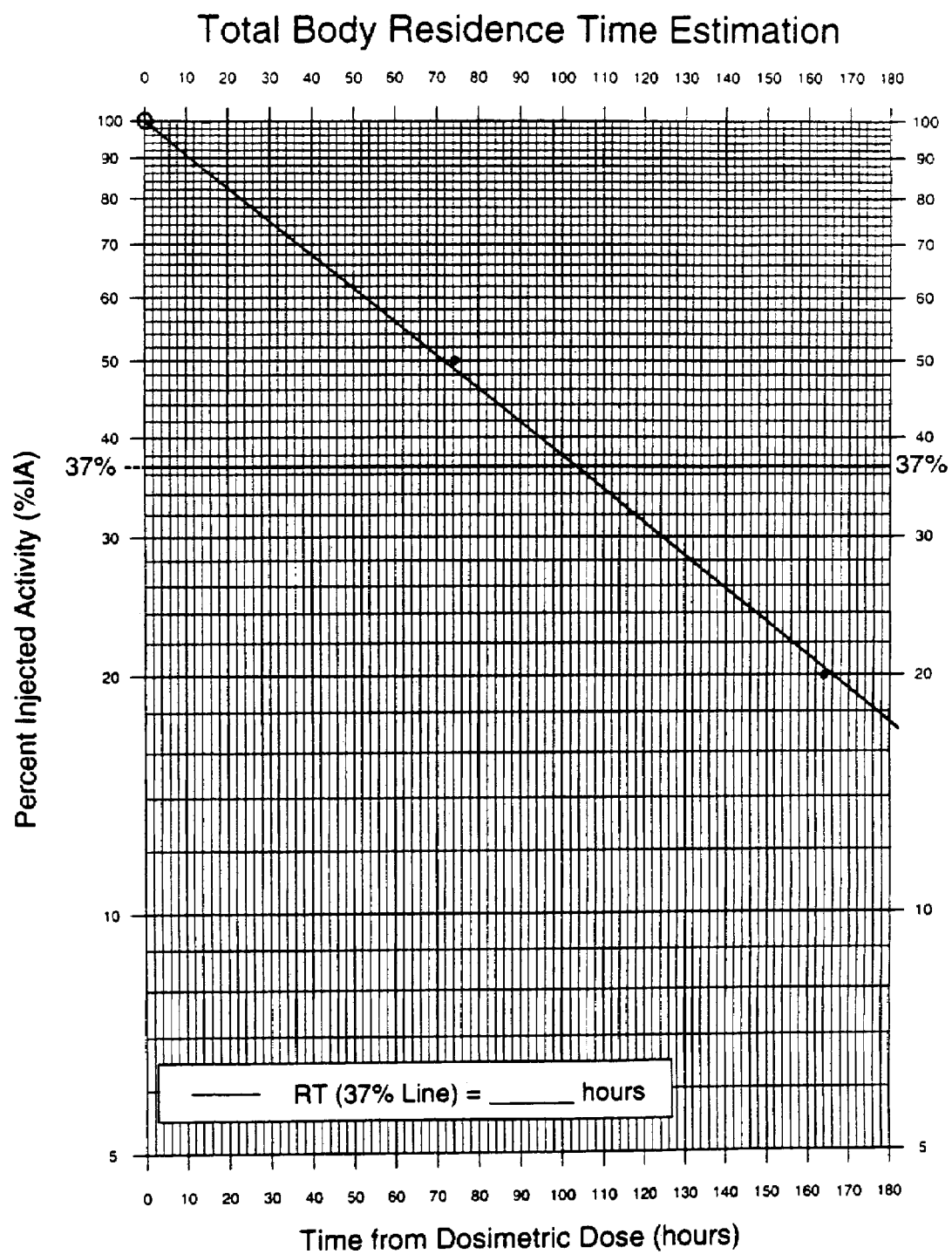
FIG. 7 is an example of a semi log paper graph for determination of total body residence time of an $^{131}$I-labeled radiopharmaceutical in a particular patient. A best fit line is drawn from the pre-plotted 100% injected activity at time 0 (point in upper left hand corner) through the plotted data points. The x-coordinate of the point where the best fit line intersects the horizontal 37% line is the total body residence time. Data and the best fit line are plotted for the sample calculation. For this example, the residence time is 103 hours.

According to a graphical method of determining the residence time, the percent injected activity remaining for each time point is then calculated by dividing the background corrected total body count from that time point by the count from Day 0 and multiplying by 100. The residence time in hours is then determined by plotting the time from the start of the infusion and the percent injected activity values for the later time points on a semi-log graph (as in FIG. 7). A best-fit line is then drawn, originating from 100% (the Day 0 value) that best fit the other plotted points. If the line does not intersect all the data points, one point should fall above the best-fit line and the other point should fall below the best-fit line. The residence time in hours is then read from the x-axis of the graph at the point where the fitted line intersects the horizontal 37% injected activity line, since by definition the residence time for a radionuclide with a monoexponential clearance pattern is equal to the time at which the percent injected activity is 37%. Even though calculation of the percent injected activity at each time point is preferred, an activity-time curve may be generated by using the raw counts at each time point or the actual activity obtained from the raw counts.

Mathematically, the residence time ($\tau$) is given by $$\tau = \frac{1}{\text{slope}} = 1.443 T_{\text{eff}}$$

where $T_{\text{eff}}$ is the effective half-life of the radionuclide. It should be noted that the individual patient's total body effective half-life, or $T_{\text{eff}}$, is quite distinct from the physical half-life of the radiopharmaceutical or, more specifically, the physical decay of the radionuclide. The $T_{\text{eff}}$ is related to the physical half-life ($T_p$) and the biological half-life ($T_b$) of the radiopharmaceutical as follows: $T_{\text{eff}}=(T_p \times T_b)/(T_p+T_b)$.

Alternatively or additionally, the residence time may be determined by substituting the times from infusions of the later data points, ($t_2$ and $t_3$ in the example below) and the background corrected counts of each data point ($C_1$, $C_2$, and $C_3$ in the example) in the following equation:

$$\text{Residence time (hr)} = \frac{t_2\left(1-\frac{C_2}{C_1}\right)}{\log_e\left(\frac{C_1}{C_2}\right)} + \frac{\frac{C_2}{C_1}(t_3-t_2)}{\log_e\left(\frac{C_2}{C_3}\right)}. \quad \text{(Equation III)}$$

The natural logarithm is denoted by $\log_e$. The formula uses log-linear interpolation over the time spanned by the data acquisition and two point log-linear extrapolation. The formula may be adjusted if additional data points are collected.

Calculation of the residence time may also be effected by using a software program to fit the percent injected activity versus time curve using the standard method of nonlinear least squares using all data points. The data are fit to the function $$\sum_{i=1}^{n} a_i e^{-\alpha_i t} \quad \text{(Equation IV)}$$

where the a's are the intercepts and the $\alpha$'s are the slopes. In the equation, n is the number of exponential terms. Therefore, for a monoexponential function, there is one slope and one intercept and the residence time is equal to $1/\alpha$ or $1/\text{slope}$, when plotted on a log-linear graph with percent injected activity plotted on the y-axis and time on the x-axis. For a biexponential function, there are two slopes and two intercepts and the residence time is equal to $$\frac{a_1/\alpha_1 + a_2/\alpha_2}{a_1+a_2}$$

when similarly plotted.

In the same manner, the residence time can be calculated for a radiopharmaceutical with a triexponential clearance pattern, etc. The residence time ($\tau$) is then obtained as follows:

$$\tau = \frac{\sum_{i=1}^{n} \frac{a_i}{\alpha_i}}{\sum_{i=1}^{n} a_i}. \quad \text{(Equation V)}$$

where $a_i$ are the intercepts and $\alpha_i$ are the slopes of the ith exponential term.

Further, several methods are available for determining residence time from graphical representations of the activity-time curve. Among these are numerical methods such as the trapezoidal rule (Bers, L., *Calculus*, Holt, Rineholt, and Winston, Inc., New York, pp. 413-416 (1969)), Simpson's rule (Macon, N., *Numerical Analysis*, Wiley, New York (1963)), and analytical methods based on the assumption that some fitting function can adequately describe the data (Riggs, D. S.,

*The Mathematical Approach to Physiological Problems*, MIT Press, Cambridge, Mass. (1976)).

Determination of the residence time of the radiopharmaceutical or analog thereof in the individual patient's body may therefore be made through (i) the use of the graphical method, (ii) the use of Equation III, or (iii) via a least squares fit or another curve-fitting program to the percent injected activity versus time curve according to Equation V, or some other method.

Furthermore, it is understood that data acquisition and calculation of the residence time for the patient may be efficiently performed through the use of an appropriate software program. For example, the software program is developed to determine the percent injected activity versus time curve and then fit these data using the standard method of nonlinear least squares using all data points, and perform the residence time calculation according to Equation V. Alternatively or additionally, software programs utilizing Equation III or the graphical method of calculating residence time (with or without a graphical display for the user) may also be developed. Preferably, the program is tailored to the particular radiopharmaceutical so that minimal input is needed to perform rapid calculations for each specific patient.

Thus, the step of determining the residence time for the radiopharmaceutical therefore usually comprises making measurements of percent injected activity of the radiopharmaceutical at each of a number of time points, the number of time points being correlated to the clearance pattern of the radiopharmaceutical, and then determining the residence time.

There should be good correlation of the dosimetric prediction of residence time with the actual residence time measured after administration of the therapeutic dose for the radiopharmaceutical. Generally, the therapeutic dose should be given within a reasonable amount of time after the dosimetric evaluation. If a substantial amount of time has passed, performance of another dosimetric evaluation is preferred to account for factors such as disease progression, human anti-mouse antibody (HAMA) responses, etc. In other words, the patient may have more disease, less disease, or have developed resistance to the antibody portion of the radiopharmaceutical at the time of treatment as compared to the time of the original dosimetric evaluation. Therefore, another dosimetric evaluation to obtain the residence time of the radiopharmaceutical in the whole body of the patient is recommended before actually treating the patient.

Calculation of the Patient-Specific Optimally Effective Dose

The patient-specific administered activity for therapy is calculated using the patient-specific total body residence time and the activity hours required to deliver a specified TBD to the patient, optionally multiplied by an attenuation factor. The following equation may be used to calculate the therapeutic dose (mCi) of the radiopharmaceutical:

$$\text{Therapeutic Dose } (mCi) = \frac{\text{Activity hours } (mCi\ hr)}{\text{Residence time } (hr)} \times \frac{\text{Desired } TBD\ (cGy)}{MTD\ cGy}. \quad \text{(Equation VI)}$$

One can solve for the appropriate therapeutic dose to be given to the individual patient by substituting in the various factors in the equation. As discussed above, most of the various factors are themselves patient-specific. The radiopharmaceutical therapy dose for an individual patient is determined from that individual's lean body mass, or M or MEM, and not the 70 kg average for men or the 56 kg average for women commonly used. Treatment can thus be tailored to the patient's size and the patient's pharmacokinetics.

A method of establishing a patient-specific optimally effective dose for administration of a radiopharmaceutical to a patient for treatment may therefore be thought of as comprising the following steps, although performing the steps in strict order as presented below is not necessary:

determining a maximum tolerated dose for the radiopharmaceutical (usually by reference to the relevant patient subpopulation), determining a desired total body dose of the radiopharmaceutical for the patient, determining the clearance profile for the radiopharmaceutical or a radiopharmaceutical analog, determining the patient's mass and maximum effective mass, selecting the lower of the patient's mass and maximum effective mass, determining the activity hours for the radiopharmaceutical or the radiopharmaceutical analog based on the lower of the patient's mass or maximum effective mass and the desired total body dose, administering a tracer dose of the radiopharmaceutical or a radiopharmaceutical analog to the patient, determining the residence time for the radiopharmaceutical or the radiopharmaceutical analog, and establishing the optimal effective activity amount, usually in mCi units, of the radiopharmaceutical for the patient by calculating the therapeutic dose based on the following equation:

$$\text{therapeutic dose} = \frac{\text{Activity Hours}}{\text{Residence time}} \times \frac{\text{desired total body dose}}{\text{maximum tolerated dose}}. \quad \text{(Equation VII)}$$

The patient-specific dosimetry taught herein is a simplified method for determining the therapeutic dose of a radiopharmaceutical to be administered to an individual patient and involves the following two steps: (a) administration of a tracer or dosimetric dose of the radiopharmaceutical or its analog followed by sequential measurement of the elimination kinetics of the tracer or dosimetric dose from the whole body, and (b) calculation of the therapeutic dose to be administered to the individual patient. The calculation may be done by a human or computer-assisted, as discussed above. Further, it may be advantageous to generate a dosimetry nomogram that takes into account the M or MEM and the residence time, and indicates the mCi amount necessary to deliver the desired TBD. The nomogram may be set up in a paper or slide rule format. The therapeutic dose can then be administered according to any appropriate protocol, e.g. immediately preceded by predosing with a non-radiolabeled form of the radiopharmaceutical or according to a prescribed schedule.

The simplified patient-specific dosimetry method is based in part on the following observations: (a) knowledge of the pattern of radioactivity clearance from the whole body for a particular radiopharmaceutical, e.g. one that takes the form of a monoexponential function allows the residence time to be graphically estimated with fewer observations, (b) the activity hours necessary to deliver a specific total body dose may be determined for a variety of body masses, (c) radiopharmaceuticals generally do not accumulate in fat tissue, (d) dose should be attenuated for reduced platelet counts or other physiological factors within the judgment of the physician, and (e) most importantly, the tracer doses predict the behavior of subsequent therapy doses.

Although subsequent treatment of the patient with the radiopharmaceutical after performance of the methods of the invention is specifically contemplated, the methods taught herein may be utilized for other purposes.

Depending on the radiopharmaceutical used, there may be little patient-to-patient variability or such variability may be safely within the acceptable range for a given treatment protocol. For this situation, it is possible to use the claimed methods on one or a few patients to establish an optimal treatment dose or dose range of the radiopharmaceutical (perhaps obtained in a mCi/kg or mCi/m² form) and thereafter to treat all patients with the dose or within the dose range elucidated through use of the methods of the invention, perhaps with slight variations due to the individual patient's characteristics such as tumor burden, body size, or blood counts.

Although treatment and pre-treatment dosimetric evaluation of humans is specifically contemplated, the methods may also find veterinary usage. Additionally, the use of an animal model may be useful to obtain information on the radiopharmaceutical and may be used in specific steps of the method, such as establishing a clearance profile or predicting a maximum tolerated dose in humans.

Computer Implementation

The invention may also be implemented in a computer system or in software. In such a case, the invention may be embodied in a computer system that is programmed or configured to execute the required methods for determining the dose of the radiopharmaceutical. Further, the invention may be embodied in a data storage device that is readable by a machine, embodying a set of instructions executable by the machine to perform the required methods of determining the dose of the radiopharmaceutical. Still further, the invention may be embodied in a computer program product comprising a computer usable medium having computer readable program code embodied therein for determining the dose of the radiopharmaceutical.

Figure 6:
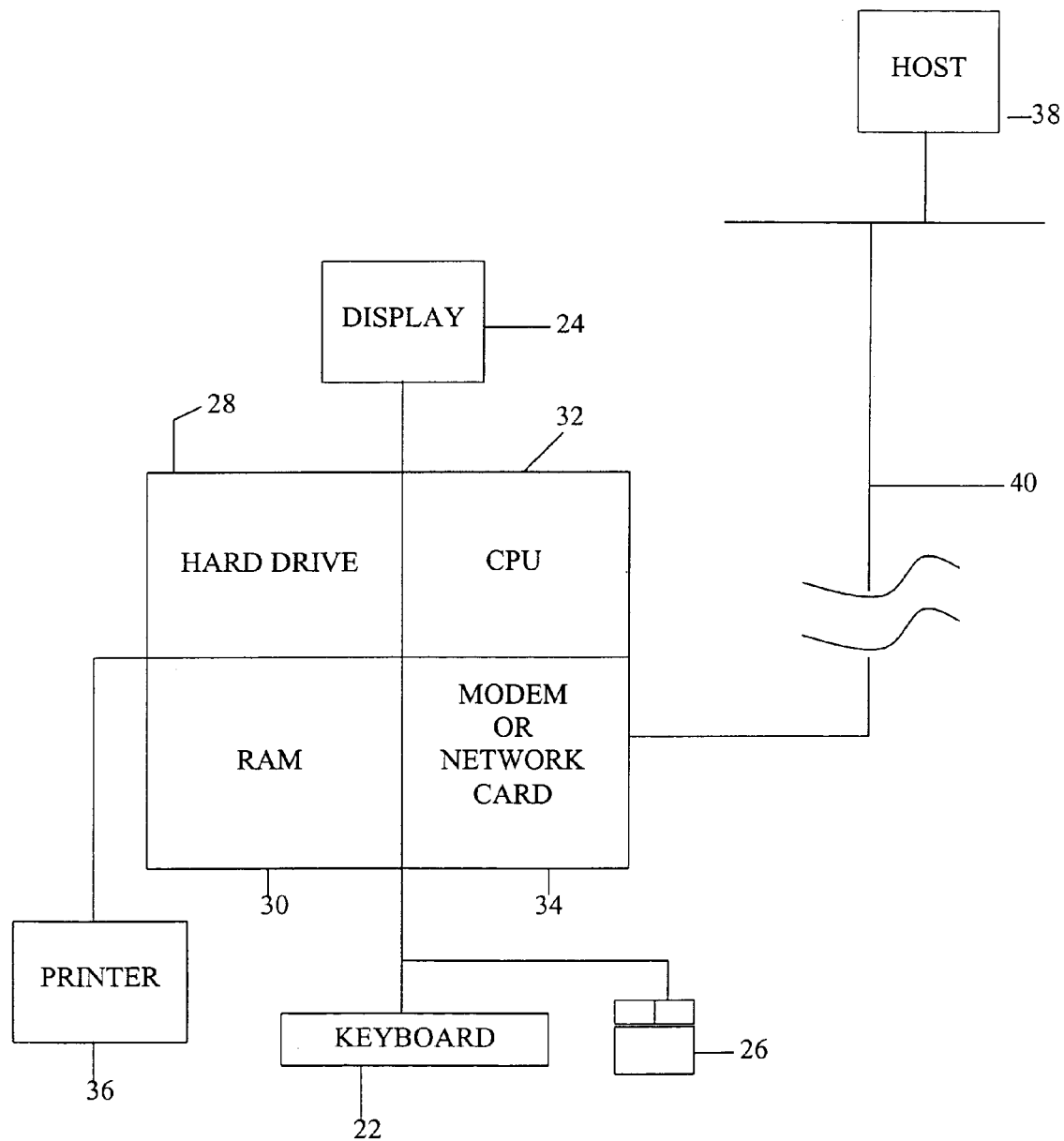
FIG. 6 is a schematic representation of a computer system for implementing the invention.

In the preferred embodiment, as shown schematically in FIG. 6, the computer system of the invention is a conventional personal computer 20 that includes, amongst other things, a keyboard 22, display 24, cursor pointing device/mouse 26, hard drive 28, RAM 30, central processing unit 32, modem or network card 34 and printer 36. The personal computer may run any one of a number of operating systems, such as Windows, Mac-OS, Linux, or Unix. The computer is programmed to execute the methods of the invention using a program written in any suitable programming language, compiled into object code if required. In the preferred embodiment, the programming is accomplished using a platform-independent programming language such as Java, running within an Internet browser environment such as Netscape Navigator or Windows Internet Explorer. Use of the Java language provides ease of distribution and updating of the program because of the platform independent nature thereof. Also, if the personal computer is connected to the Internet, the method can be run as an "applet" of program instructions that is downloaded as required from a host computer 38 via the Internet or other network 40 into the computer data storage device (RAM 30 or hard drive 28). The "applet" (or other software) is transmitted from the host computer embodied in an analog and/or digital carrier wave that is read by the computer to extract the "applet" from the carrier wave.

It will of course be appreciated that any suitable general purpose or dedicated computing device running appropriate software or firmware may be used.

The computer 20 receives instructions for implementing the method of the invention from the data storage device (for example the hard drive 28 or other magnetic storage medium, CD-ROM or other optical storage medium, ROM, RAM 30 or other electronic storage medium, or any other data storage device) that is readable by the computer 20. The data storage device embodies a set of instructions executable by the computer to perform the methods of determining the dose of the radiopharmaceutical as described below. Still further, the invention may be embodied in a computer usable medium (for example a data storage device, an analog or digital carrier wave or a printed medium) having computer readable program code embodied therein for determining the dose of the radiopharmaceutical according to the method described below.

The preferred method of determining the dose of the radiopharmaceutical is shown in flowchart form in FIGS. 2-5. The flowchart is applicable to the computer system of the invention, the data storage device of the invention, and the computer usable medium of the invention.

At the commencement of the computer-implemented method, the user selects which radiopharmaceutical treatment is to be administered to the patient, step 110.

Then, patient-specific data is entered by the user, step 120. As illustrated, this includes patient mass, height and gender, but further details such as patient name, age and health insurance details are typically also entered. The data are typically gathered over a number of days. Accordingly, in the preferred implementation of the method, a record is created for each patient, which can then be updated as new data is gathered, until the method is complete.

After the patient-specific data is gathered, the patient's MEM is determined from the patient's height and gender, step 130. This may be done from separate databases or tables of MEM vs. patient height for men and women (see Table 1, e.g.) or alternatively a formula may be used.

Then it is determined whether the patient mass is greater than the MEM, step 140. If so, the mass (M) to be used in the method is set equal to the maximum effective mass, step 150. If not, the mass M is set equal to the patient mass, step 160.

At step 170, the required activity hours to deliver a Maximum Tolerated Dose for the procedure is determined from the mass M. This is again typically done using a table or database (see Table 2, e.g.), or a formula, or a combination.

Figure 3:
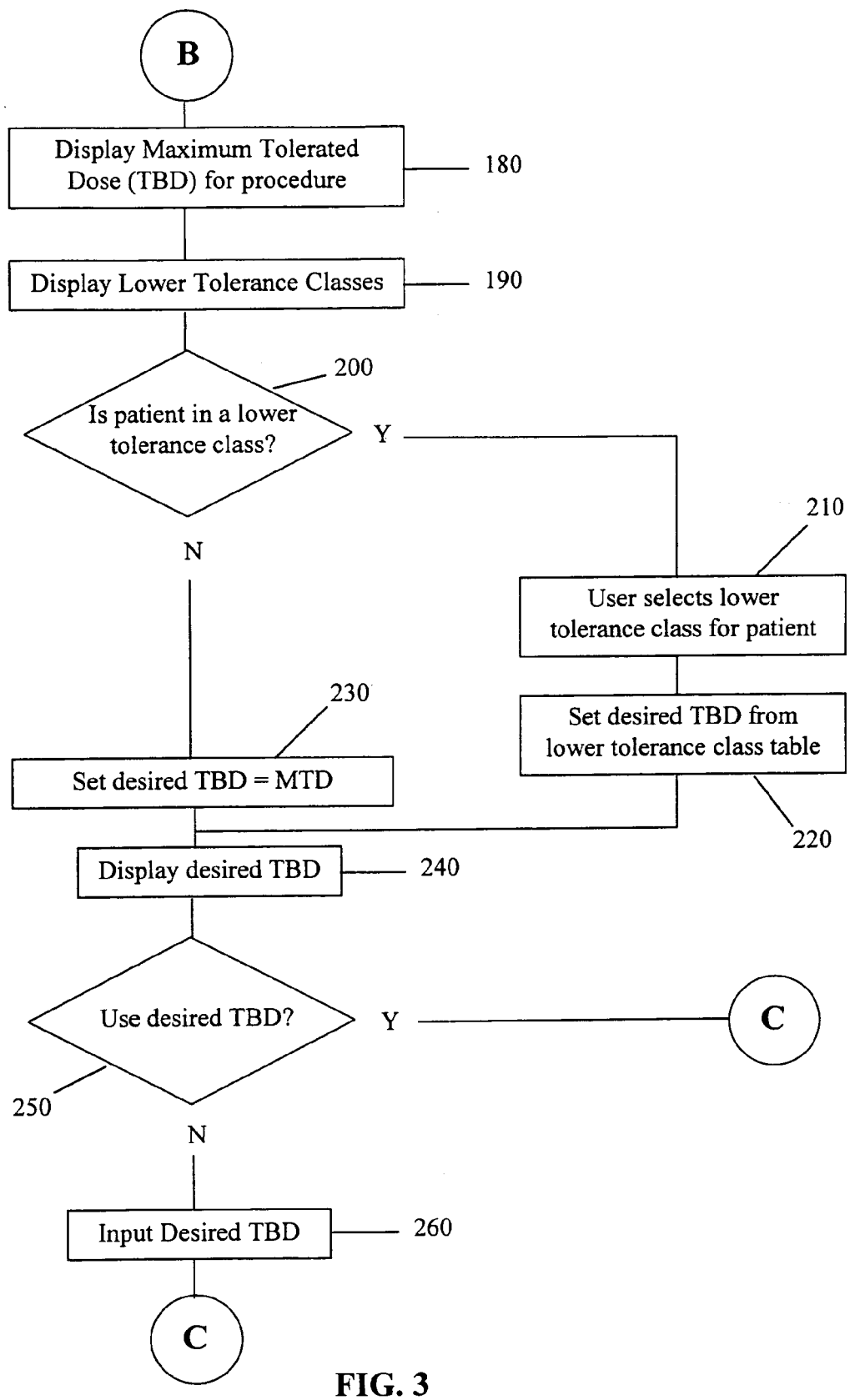
FIG. 3 is a flowchart for the implementation of the methods of the invention in a computer system.

Turning now to FIG. 3, the Maximum Tolerated Dose for the procedure is displayed, step 180, and classes of patients who have a lower tolerance to the treatment are displayed, step 190. The user then selects whether or not the patient is in a lower tolerance class, step 200.

If the patient is in a lower tolerance class, the user selects the lower tolerance class to which the patient belongs, step 210, and the desired Total Body Dose is set for the patient from a table of lower tolerance classes vs. Total Body Doses, step 220.

If the patient is not in a defined lower tolerance class, the desired Total Body Dose is set equal to the Maximum Tolerated Dose, step 230.

The desired Total Body Dose is then displayed to the user, step 240, and confirmation is requested from the user as to whether or not this desired Total Body Dose is to be used, step 250. If, in the discretion of the user (typically a physician), the displayed Total Body Dose is not to be used, the desired Total Body Dose is input by the user, step 260.

Figure 4:
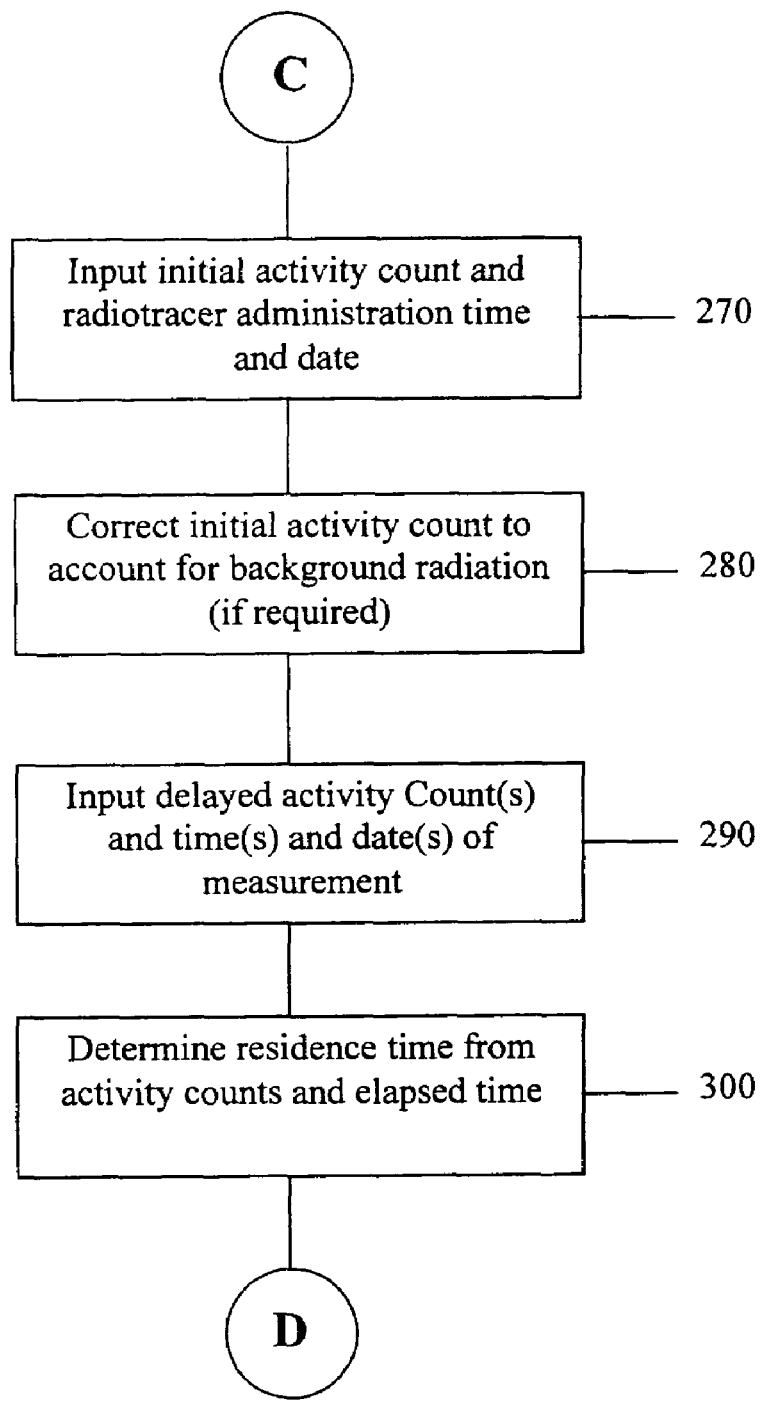
FIG. 4 is a flowchart for the implementation of the methods of the invention in a computer system.

Turning now to FIG. 4, the initial radiotracer activity count and the date and time of day are entered, step 270. This entry may be a single activity count, or it may take the form of a number of readings (e.g. anterior scan reading, posterior scan reading, anterior background reading, posterior background reading,) which are then subtracted and meaned as described above (by the computer system) to provide a background corrected activity count reading, step 280. The entry of date and time is also optional, but is strongly preferred for record keeping and also to allow the computer itself to calculate the elapsed times between subsequent readings. If the intial date and time are not entered, the initial activity counts are considered to have been taken at zero elapsed time.

Then the subsequent activity counts and dates and times are entered, step 290. As for the initial activity counts, these entries may be single activity counts, or they may take the form of a number of readings (e.g. anterior scan reading, posterior scan reading, anterior background reading, posterior background reading,) which are then subtracted and meaned as described above (by the computer system) to provide a background corrected activity counts. Also, as an alternative to the entry of dates and times, subsequent readings may be based on entry of elapsed time. Again, the preferred method is the entry of date and time, for record keeping and to reduce errors in the calculation of elapsed times. If date and time entries are used, the computer calculates the elapsed time for the subsequent activity counts. In the preferred embodiment, at least two subsequent activity counts are conducted, and the residence time is calculated.

The residence time is then calculated from the formula for residence time set out above, or by using a curve fit to the data, also as set out above, step 300. In the preferred embodiment, the residence time is based on the initial activity count (100% activity), two subsequent activity counts, and a 37% injected activity level, which is equal to the residence time, but this can be varied according to the particular treatment.

Figure 5:
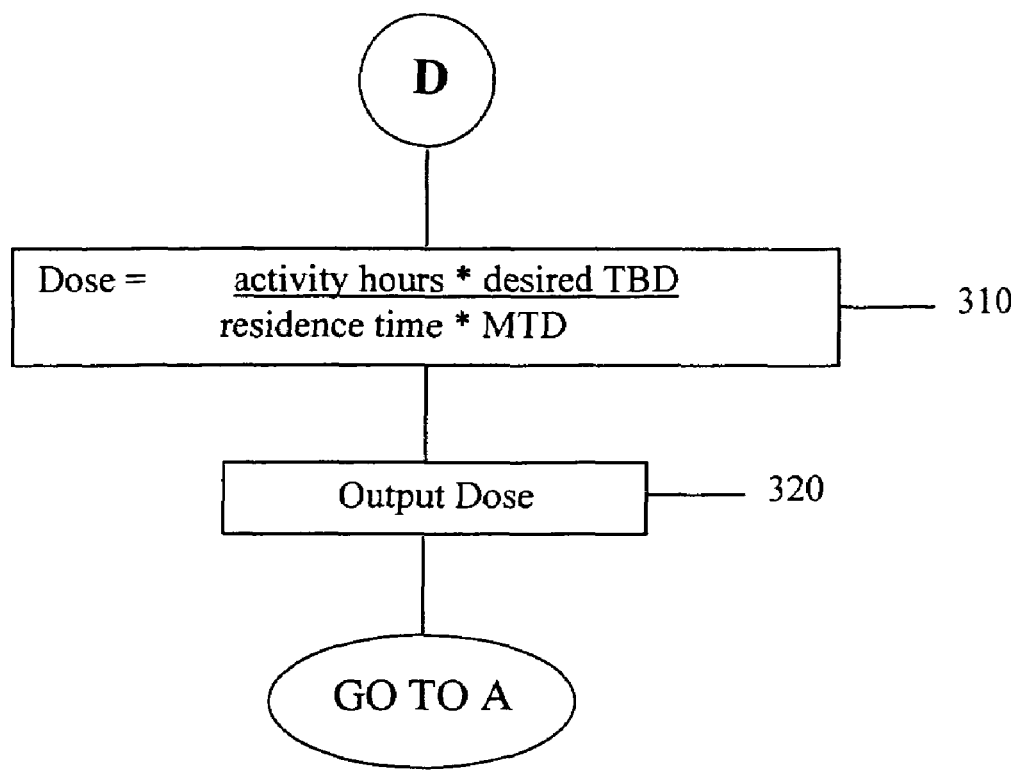
FIG. 5 is a flowchart for the implementation of the methods of the invention in a computer system.

Turning now to FIG. 5, the therapeutic dose is calculated from the calculated activity hours, the residence time, the desired Total Body Dose and Maximum Tolerated Dose, step 310.

The therapeutic dose is then provided to the user as an output, step 320. This can be done by means of the display 24, the printer 36, or another output device. Alternatively, the output and other data may be transmitted over the network or Internet 40 for use at the host 38 or at another location.

While the computer and software implemented method has been described in the flowchart in a linear manner in a particular order, it will be appreciated that the order of the steps in the flowchart can be varied, and the user of the system may be permitted to jump between various steps to permit the entry and amendment of data as necessary. In particular, the user may be presented with a display in the form of a table or spreadsheet into which the data are entered. Also, while the data are entered manually in the described embodiment, in an alternative embodiment the data are captured directly from the gamma camera or other imaging device, so that the software operates on a signal that is directly related to the physical parameter of the activity of the radiotracer in the patient.

Also, the data captured may be more extensive than described above. For example, the particular details of the gamma camera (name, collimator, camera height from table, body scan field of view, body scan speed, calibration details) or other details of the procedure may be captured to permit further analysis.

Further, a graph of the percentage activity vs. the time from the initial dose may be displayed to the user, with the data points shown together with or without a fitted curve. The user can then use their judgement or estimation to verify or select the residence time.

Still further, the software may provide a preliminary estimate of the residence time after only the first subsequent activity count has been taken. This preliminary estimate of the residence time can then be used to provide a preliminary estimate of the required dose. If this preliminary estimate of the required dose exceeds the volume of the supplied vial of the therapeutic radiopharmaceutical, the software provides a warning to the user that another vial of the radiopharmaceutical may be required in the therapeutic procedure.

Finally, the software will include typical range constraint checking for the entered data. For example, if the patient's weight is below 75 lb. or above 300 lb., a confirmation is required. Similarly, the user will be notified if the time lapse between initial and subsequent counts is outside expected ranges, or the activity counts show an increase with passing time, or the day/date entries are not in the required format.

The invention now being generally described, the same will be better understood by reference to the following detailed example, which is offered for illustration only and is not to be consdidered limiting of the invention unless otherwise specified.

EXAMPLE

A radioimmunotherapy method utilizing $^{131}$I-labeled Anti-B1 (murine anti-CD20) monoclonal antibody as the radiopharmaceutical is useful for treatment of non-Hodgkin's lymphoma. A fundamental consideration with the anti-CD20 monoclonal antibody is that the antibody while binding with high affinity to malignant cells of non-Hodgkin's lymphoma, also cross-reacts with normal circulating B cells in the blood and with normal splenic B cells. Due to this cross-reactivity, the variable B-cell population, and the preferred radioimmunotherapy protocol with a dose ranging design in which patients receive varying amounts of unlabeled antibody prior to the administration of the radiolabeled antibody, it was expected (and subsequently observed) that there would be substantial patient-to-patient variability in the rate of clearance of the radiopharmaceutical from the body. Thus, with varying clearance rates of the $^{131}$I-labeled Anti-B1 antibody radiopharmaceutical, differing radiation doses would be delivered per millicurie administered, even if patients had identical masses or body surface areas. Therefore, optimization of the treatment dose on a patient-specific basis through the methods of the present invention provides significant advantages.

A dose escalation study was performed previously in a range of 25 cGy up to 85 cGy (as described in Kaminski, M. S. et al., "Iodine-131-Anti-B1 Radioimmunotherapy for B-cell Lymphoma," *J. Clin. Oncol.*, 14:1974-1981 (1996)). From this study, it was determined that in patients who had not previously received a bone marrow transplant, the MTD was 75 cGy. The desired TBD was therefore set at 75 cGy for the majority of patients (having a baseline platelet count of $\geq$150,000 cells/mm$^3$) and set at 65 cGy for patients with a baseline platelet count greater than 100,000 and less than 150,000 cells/mm$^3$. The lower desired TBD for the subgroup was set after a higher frequency of hematologic toxicity was noted in patients with reduced platelet count.

Gamma cameras had either a single-head or dual-head configuration with a large or an extra large field of view and were equipped with a medium- or high-energy parallel hole collimator suitable for performing whole body scans and whole body counts with $^{131}$I. A 5×10$^6$ count $^{99m}$Tc extrinsic flood image using the $^{131}$I collimator(s) was obtained at some point before using gamma camera images for dose calculations. Camera extrinsic uniformity with the $^{131}$I collimator was assessed periodically using $^{99m}$Tc or $^{57}$Co as a source with imaging at the appropriate window. Inspection for collimator defects was visual. An intrinsic $^{131}$I flood image of 5×10$^6$ counts was also performed. The dose calibrator used for dispensing patient doses was calibrated (checked for constancy) each day that it was used to quantitate radioactivity. Calibration with a National Institute of Standards and Technology (NIST)-traceable $^{131}$I source was performed on a daily basis in addition to routine quality control of accuracy and linearity.

Camera sensitivity was performed each day prior to obtaining the patient whole body counts. A liquid source of a calibrated amount of $^{131}$I (typically 200-250 μCi initial activity) was scanned to determine the counting efficiency (background corrected CPM/μCi). This was performed to assure that the same collimator, scanning speed, window setting, and geometry was maintained at each imaging time point.

Anterior and posterior NaI probe counts (collimated thyroid uptake probe) at 2.5 meters from the patient were acquired for 1 minute per view with the patient seated on a stool. One minute background counts were also taken at each measurement time. The photopeak was centered at 364 keV with a symmetric window of 314 to 414 keV. The probe was pointed midway between the patient's umbilicus and xyphoid. Patient counts were acquired immediately post infusion (within 1 hr) of the radiopharmaceutical (in a 5 mCi amount for dosimetry) before voiding (to determine 100% infused activity), then daily for 5 to 8 days (these latter counts were acquired after voiding). Probe response as a function of various positions of a point source of $^{131}$I was measured at 2.5 meters from the probe. Results show that the probe used in this study had a response of ±10% over a circular diameter of 25 inches with the source centered in the probe field-of-view at 2.5 meters. Routine clinical quality control procedures for the probe involved daily counts from a Ba-133 source of known activity. Ba-133 quality control data showed counts generally were within ±2% of the expected counts.

Whole body imaging was performed immediately after room background determination. The prepared tracer activity was measured in a dose calibrator and recorded. The diagnostic scans were obtained at three time points (Day 0; Day 2, 3, or 4; and Day 6 or 7 post-infusion). The computer and gamma camera for whole body scans and background were as follows:

Medium- or high energy parallel hole collimator
Symmetric window centered on the 364 keV photopeak of $^{131}$I (314-414 keV)
Matrix: minimum 128×128
Scan speed: 30 cm/min.

Background counts were taken immediately after the quality control procedure and before the patient entered the room (while the patient was a considerable distance from the room). The average background rate for a particular gamma camera and collimator were established. If abnormal high or low background counts were measured, reasons for variation (appropriate set-up or identification of other radioactive sources) were assessed and corrective actions were performed. The same region of interest used for patient counts was used for the background counts.

Anterior and posterior whole body images were obtained. For any particular patient, the same gamma camera, collimator, and scanning speed were used for all scans. Extremities were included in the images and the arms were not allowed to cross over the body. The camera head(s) were brought as close to the patient as possible; the posterior view was obtained with the camera head directly below the imaging table. The scans were centered on the midline of the patient. A rectangular ROI was drawn around the entire field of view to obtain separate anterior ($C_a$) and posterior ($C_p$) counts. The time of the images and the total body counts were recorded.

The patient is a 63-year-old, 5' 6" man weighing 90 kg. His baseline platelet count is 121,000 cells/mm$^3$ and his % injected activities from 1, 72, and 164 hr were 100%, 50%, and 20%, respectively. From Table 1, his maximum effective mass is determined to be 88.5 kg. Because his maximum effective mass is less than his actual mass, the maximum effective mass is used to look up the value for activity hours from Table 2. The activity hours are 9490 mCi·hr. By plotting the % injected activity values on FIG. 7, the residence time is determined to be 103 hours. As the patient's platelet count is greater than 100,000 and less than 150,000 cells/mm$^3$, the desired TBD is 65 cGy. The equation for the therapeutic dose (mCi) is then solved as follows:

$$\text{Therapeutic Dose } (mCi) = \frac{9490 \text{ } mCi \text{ h}}{103 \text{ h}} \times \frac{65 \text{ } (cGy)}{75 \text{ } cGy}$$

$$= 80 \text{ } mCi$$

$^{131}$I – Labeled Radiopharmaceutical

The patient is therefore given 80 mCi of the radiopharmaceutical at the treatment stage.

Notably, a 75 cGy dose target of this radiopharmaceutical often resulted in therapeutic doses ranging from 58 to 149 mCi for a group of patients treated, thereby demonstrating the need for the patient-specific dosimetry method of the present invention.

In summary, the patient-specific whole body dosimetric approach assumes uniform deposition of activity in an ellipsoid to approximate the patient's biodistribution. While not fully capable of dealing with heterogeneous distribution of tracer activity, the simplicity of the approach, coupled with its ease of use make it attractive as a clinically realistic method for prospectively determining the millicurie dose for treatment of a given patient with a radiopharmaceutical.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

The invention claimed is:

1. A method of establishing a patient-specific therapeutic dose for administration of an $^{131}$I-labeled anti-B1 antibody radiopharmaceutical to a patient, the method comprising:
   determining a maximum tolerated dose for the radiopharmaceutical;
   determining a desired total body dose (TBD) of the radiopharmaceutical for the patient;
   administering to the patient a trace dose of a radiopharmaceutical or an analog of the radiopharmaceutical;
   determining a clearance profile for the radiopharmaceutical or a radiopharmaceutical analog;

determining that the patient's mass is higher than the patient's maximum effective mass (MEM);

determining the activity hours (AH) for the radiopharmaceutical or radiopharmaceutical analog with the following equation (Equation I):

$$AH = \frac{TBD \times (MEM)}{\left[\sum_{elec} \Delta_{elect} + \sum_{phot} \Delta_{phot} \phi_{phot}^{TB}\right]} \text{ where} \quad \text{(Equation I)}$$

$$\left[\sum_{elec} \Delta_{elect} + \sum_{phot} \Delta_{phot} \phi_{phot}^{TB}\right]$$

in Equation 1 represents the sum of electron energy and photon energy deposited in the total body of the patient by the radiopharmaceutical or radiopharmaceutical analog and said determining activity hours uses the patient's maximum effective mass (MEM);

determining residence time of said administered trace dose of the radiopharmaceutical or the radiopharmaceutical analog in the whole body of the patient, the residence time being correlated to the clearance profile; and establishing the patient-specific dose of the radiopharmaceutical for the patient by solving for therapeutic dose in the following equation:

therapeutic dose=Activity Hours/Residence time× desired total body dose/maximum tolerated dose.

2. A method according to claim 1, wherein the step of determining the activity hours via Equation 1 comprises performing obtaining activity hours from a table or database that has been prepared using Equation 1.

3. A method according to claim 1, wherein the step of determining the maximum tolerated dose comprises performing a dose escalation study for the radiopharmaceutical in a patient population.

4. A method according to claim 1, wherein the maximum effective mass is based solely on the gender and height of the patient.

5. A method according to claim 1, wherein the step of determining the clearance profile comprises performing a study following measurement over time of the loss of radioactivity from an administered radiopharmaceutical.

6. A method according to claim 1, wherein the step of determining the clearance profile comprises performing a dose escalation study for the radiopharmaceutical.

7. A method according to claim 1, wherein the clearance profile provides an activity-time curve shape for the radiopharmaceutical.

8. A method according to claim 1, wherein the step of determining the residence time for the radiopharmaceutical comprises:

making measurements of radioactivity in the whole body of the patient at each of a number of time points, calculating percent injected activity of the radiopharmaceutical at each of the time points, and establishing the residence time by plotting the time points vs. percent injected activity on a semilog graph and determining the time at 37% injected activity.

9. A method of claim 8, wherein the measurements of each time point is background corrected.

10. A method of claim 8, wherein the number of time points are correlated to the clearance profile of the radiopharmaceutical so that at least 2 measurements are made if the radiopharmaceutical has monoexponential clearance, at least 4 measurements are made if the radiopharmaceutical has biexponential clearance, and at least 6 measurements are made if the radiopharmaceutical has triexponential clearance.

11. A method according to claim 1, wherein the step of determining the residence time for the radiopharmaceutical comprises:

making measurements of radioactivity in the whole body of the patient at each of three time points and solving in the following equation:

$$\text{Residence time}(hr) = \frac{t_2\left(1 - \frac{C_2}{C_1}\right)}{\log_e\left(\frac{C_1}{C_2}\right)} + \frac{\frac{C_2}{C_1}(t_3 - t_2)}{\log_e\left(\frac{C_2}{C_3}\right)}$$

where $t_1$, $t_2$, and $t_3$ are the three time points and $c_1$, $c_2$, and $c_3$ are the counts at each of the $t_1$, $t_2$, and $t_3$ time points.

12. A method according to claim 1, wherein the step of determining the residence time for the radiopharmaceutical comprises:

making measurements of radioactivity in the whole body of the patient at each of a number of time points, and solving for τ in the following equation:

$$\tau = \frac{\sum_{i=1}^{n} \frac{a_i}{\alpha_i}}{\sum_{i=1}^{n} a_i}$$

where τ is residence time, n is the number of exponential terms as determined by the clearance profile, $a_i$ are the intercepts, and $\alpha_i$ are the slopes of the ith exponential term when plotted on a log-linear graph with percent injected activity plotted on the y-axis and time on the x-axis.

13. A method of claim 12, wherein the number of time points are correlated to the clearance profile of the radiopharmaceutical so that at least 2 measurements are made if the radiopharmaceutical has monoexponential clearance, at least 4 measurements are made if the radiopharmaceutical has biexponential clearance, and at least 6 measurements are made if the radiopharmaceutical has triexponential clearance.

14. A method according to claim 1, wherein the step of determining the residence time for the radiopharmaceutical comprises:

making measurements of radioactivity in the whole body of the patient at each of a number of time points, generating an activity-time curve, and using the trapezoidal rule or Simpson's rule to determine the residence time.

15. A method according to claim 1, wherein said maximum effective mass is a multiple of a calculated lean body mass, said multiple having been determined from empirical data gathered from dose escalation studies in a patient population to which said patient belongs.

16. A method according to claim 15, wherein said multiple is 1.37.

17. A method of establishing a patient-specific dose for administration of an $^{131}$I-labeled anti-B1 antibody radiopharmaceutical to a patient, the method comprising:

determining a clearance profile for the radiopharmaceutical or a radiopharmaceutical analog, said clearance profile providing a minimum number of time points for determination of the patient-specific residence time of the radiopharmaceutical or the radiopharmaceutical analog;

determining the desired total body dose (TBD) of the radiopharmaceutical for the patient;

determining that the patient's mass (M) is higher than the patient's maximum effective mass (MEM);

determining the activity hours (AH) for the radiopharmaceutical or a radiopharmaceutical analog by with Equation I using the patient's maximum effective mass (MEM):

$$AH = \frac{TBD \times (MEM)}{\left[\sum_{elec} \Delta_{elect} + \sum_{phot} \Delta_{phot} \phi_{phot}^{TB}\right]} \text{ where} \quad \text{(Equation I)}$$

$$\left[\sum_{elec} \Delta_{elect} + \sum_{phot} \Delta_{phot} \phi_{phot}^{TB}\right]$$

in Equation 1 represents the sum of electron energy and photon energy deposited in the total body of the patient by the radiopharmaceutical or radiopharmaceutical analog;

determining the patient-specific residence time of an administered tracer dose of the radiopharmaceutical or the radiopharmaceutical analog in the whole body of the patient; and establishing a therapeutic dose of the radiopharmaceutical for the patient by dividing the activity hours by the patient-specific residence time to obtain an initial therapeutic dose and optionally multiplying the initial therapeutic dose by an attenuation factor, said attenuation factor being determined by the TBD divided by the maximum tolerated dose for the radiopharmaceutical.

18. A method according to claim 17, wherein the step of determining the residence time for the radiopharmaceutical comprises:

making measurements of radioactivity in the whole body of the patient at each of a number of time points, and solving for τ in the following equation:

$$\tau = \frac{\sum_{i=1}^{n} \frac{a_i}{\alpha_i}}{\sum_{i=1}^{n} a_i}$$

where τ is residence time, n is the number of exponential terms as determined by the clearance profile, $a_i$ are the intercepts, and $\alpha_i$ are the slopes of the ith exponential term when plotted on a log-linear graph with percent injected activity plotted on the y-axis and time on the x-axis.

19. A method according to claim 18, wherein the number of time points are correlated to the clearance profile of the radiopharmaceutical so that at least 2 measurements are made if the radiopharmaceutical has monoexponential clearance, at least 4 measurements are made if the radiopharmaceutical has biexponential clearance, and at least 6 measurements are made if the radiopharmaceutical has triexponential clearance.

20. A computer system for use in determining a desired dose of a radiopharmaceutical to be administered to a patient, comprising:

an input device adapted to receive (a) an input of at least a patient's maximum effective mass, which is lower than said patient's mass, (b) an input of an initial activity count of a radiotracer, and (c) an input of at least one subsequent activity count of the radiotracer;

a central processing unit adapted to determine (a) an activity hour parameter from said input of said at least the patient's maximum effective mass to provide a maximum tolerated dose of the radiopharmaceutical, (b) a residence time of the radiopharmaceutical from said inputs of said initial activity count and said at least one subsequent activity count by fitting a curve to the initial activity count and the at least one subsequent activity count, graphically displaying the curve for the user, and solving the curve for the residence time, and (c) a patient-specific dose of the radiopharmaceutical from said residence time and activity hour parameter determinations; and an output device adapted to provide a graphical display of said curve and said patient-specific dose.

21. A computer system according to claim 20 wherein said central processor is adapted to determine the maximum effective mass from a table of maximum effective mass versus patient height.

22. A computer system according to claim 20, wherein said central processing unit uses a least squares fit numerical method to fit the curve.

23. A computer system according to claim 20, wherein said output is adapted to generate a warning that an additional vendor-provided dose is required if said central processing unit determines that said patient specific dose exceeds a vendor-provided dose.

24. A computer system according to claim 20, wherein said central processing unit is adapted to determine the maximum effective mass from a formula of maximum effective mass versus patient height.

25. A computer system according to claim 20, further comprising a database of activity hour parameters particular maximum tolerated doses and particular patient parameters, wherein said central processing unit utilizes said database to determine the activity hour parameter.

26. A computer system according to claim 20, wherein said central processing unit is adapted to correct said inputs of said initial and subsequent activity counts to take into account background radiation.

27. A computer system according to claim 26, wherein said input device is adapted to receive a background radiation count and wherein said central processing unit corrects for background radiation by subtracting the background radiation count from a corresponding one of said initial and subsequent activity counts.

28. A computer system according to claim 27, wherein said input device is adapted to receive an input of a plurality of activity counts and an input of a plurality of related background radiation counts, and wherein said central processing unit is adapted to determine a plurality of intermediate corrected activity counts from the activity counts and the related background radiation counts and to determine a corrected activity count as a mean of the intermediate corrected activity counts.

* * * * *

UNITED STATES PATENT AND TRADEMARK OFFICE
CERTIFICATE OF CORRECTION

PATENT NO. : 7,668,662 B2 Page 1 of 1
APPLICATION NO. : 11/200688
DATED : February 23, 2010
INVENTOR(S) : Kroll et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1043 days.

Signed and Sealed this

Seventh Day of December, 2010

David J. Kappos
*Director of the United States Patent and Trademark Office*